United States Patent [19]

Akasaka et al.

[11] Patent Number: 5,475,014
[45] Date of Patent: Dec. 12, 1995

[54] OXAZOLIDONE DERIVATIVE

[75] Inventors: Kozo Akasaka; Akiharu Kajiwara; Satoshi Nagato; Youichi Iimura; Ichirou Yoshida; Atsushi Sasaki; Masanori Mizuno; Atsuhiko Kubota; Takaki Kagaya; Mariko Komatsu, all of Ibaraki, Japan

[73] Assignee: Eisai Co., Ltd., Tokyo, Japan

[21] Appl. No.: 204,326

[22] Filed: Mar. 8, 1994

[30] Foreign Application Priority Data

Oct. 23, 1991 [JP] Japan .................. 3-275526
Sep. 4, 1992 [JP] Japan .................. 4-236642

[51] Int. Cl.$^6$ .................. C07D 417/10; A61K 31/425
[52] U.S. Cl. .................. 514/367; 514/321; 546/198; 548/161; 548/178
[58] Field of Search .................. 548/178, 161; 546/198; 514/321, 367

[56] References Cited

U.S. PATENT DOCUMENTS 4,801,600  1/1989  Wang .................. 548/232
5,322,835  6/1994  Takahashi .................. 504/225

*Primary Examiner*—Robert Gerstl
*Attorney, Agent, or Firm*—Flynn, Thiel, Boutell & Tanis

[57] ABSTRACT

An oxazolidone derivative represented by formula (I) which has a monoamine oxidase inhibition effect:

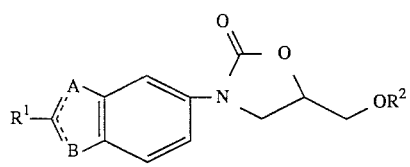

(I)

{wherein A and B each represents a nitrogen atom, a sulfur atom or an oxygen atom, with the proviso than at least one of A and B must be a nitrogen atom, $R^1$ represents a group of the formula:

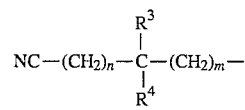

(in which n and m each represents 0 or an integer of 1 to 4, and $R^3$ and $R^4$ each represents a hydrogen atom, a hydroxyl group, a lower alkyl group, etc. ), a group represented by the formula:

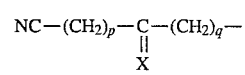

(in which p and q each represents 0 or an integer of 1 to 4 and X represents an oxygen atom, sulfur atom, etc.) and a group represented by the formula:

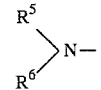

$R^2$ represents a hydrogen atom or a lower alkyl group}.

24 Claims, No Drawings

OXAZOLIDONE DERIVATIVE

This application is a 371 of PCT/JP2/01257 filed Sep. 30, 1992.

FIELD OF INDUSTRIAL APPLICATION

The present invention relates to oxazolidone derivatives having an excellent medicinal effect.

BACKGROUND OF THE INVENTION

It is said that one out of 20 to 30 people suffer from depression including mild cases. Further, many people are troubled with a depressive state which is one of the after effects of cerebrovascular lesion or the like. The depressive state and depression can be thus counted among modern diseases.

For the remission of depression or depressive state, tricyclic antidepressants such as imipramine and amitriptyline have been used heretofore. However, tricyclic antidepressants are not preferred, since they are not effective on nearly 40% of the patients and have harmful side effects which hinder their administration to, particularly, aged people, such as tachycardia, hypotension, headache, finger trembling, constipation and dysuria.

On the other hand, it is known from old times that monoamine oxidase (hereinafter referred to as MAO) inhibitors have an antidepressant effect and it has been pointed out that the range of their effect thereof is wider than that of the tricyclic antidepressants. However, hydrazide MAO inhibitors are now not used, since it was found that they caused hepatic disorders, while non-hydrazide MAO inhibitors have come to be scarcely used, since their MAO inhibition effect is irreversible.

After further investigations, it has been found that MAO is classified into two types, i.e. types A and B, and that harmful side effects such as orthostatic hypotension, headache and dizziness and the so-called cheese effect which causes a hypertensive fit by the interaction with foods having a high tyramine content are caused mainly by the MAO-B inhibition effect.

After extensive investigations made for the purpose of finding functions showing reversible effects while being free from serious harmful side effects or interaction with foods and effective on patients in a wide range under these circumstances, the inventors have noted a MAO-A inhibition effect and made further investigations on compounds having such an effect.

As a result, the inventors have found that the object can be attained by oxazolidone derivatives which will be described below. The present invention has been completed on the basis of this finding.

Although oxazolidone derivatives useful as medicines are disclosed in, for example, Japanese Patent Publication-B Nos. 40428/1985, 5391/1988, 54710/1988, 63671/1988, 56071/1989, 37354/1990, 61465/1990 and 9106/1991 and Japanese Patent Publication-A No. 63671/1988, they are different from the compounds of the present invention in the structure.

DISCLOSURE OF THE INVENTION

The present invention provides an oxazolidone derivative represented by the following general formula (I) or a pharmacologically acceptable salt thereof:

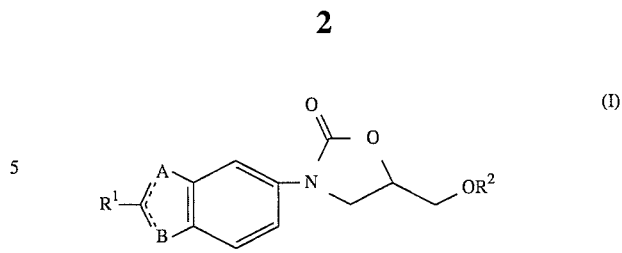

{wherein A and B each represents a nitrogen atom, a sulfur atom or an oxygen atom, with the proviso that at least one of A and B must be a nitrogen atom, $R^1$ represents a hydrogen atom, a halogen atom, a cyano group, a lower alkyl group, a cycloalkyl group, a hydroxyalkyl group, an alkoxyalkyl group, a cyanoalkenyl group, a group represented by the formula:

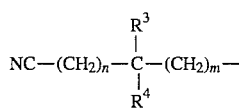

[in which n and m each represents 0 or an integer of 1 to 4, and $R^3$ and $R^4$ may be the same or different from each other and each represents a hydrogen atom, a hydroxyl group, a lower alkyl group, a lower alkoxyl group, or a group represented by the formula:

(in which $R^7$ and $R^8$ may be the same or different from each other and each represents a hydrogen atom or a lower alkyl group, or $R^7$ and $R^8$ may form a ring together with the nitrogen atom to which they are bonded and the ring may be substituted)], a group represented by the formula:

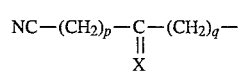

[in which p and q each represents 0 or an integer of 1 to 4 and X represents an oxygen atom, a sulfur atom or a group represented by the formula: $=N-OR^9$ ($R^9$ being a hydrogen atom or a lower alkyl group)], a group represented by the formula:

(in which $R^5$ and $R^6$ may be the same or different from each other and each represents a hydrogen atom, a lower alkyl group or a cyanoalkyl group, or $R^5$ and $R^6$ may form a ring together with the nitrogen atom to which they are bonded and the ring may be substituted), a group represented by the formula:

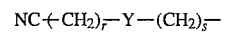

(in which r and s each represents 0 or an integer of 1 to 4, and Y represents an oxygen atom, a sulfur atom, a group of the formula: —NH—), an aryl group which may be substituted, an arylalkyl group which may be substituted, a heteroaryl group which may be substituted, a heteroarylalkyl group which may be substituted, a carbamoylalkyl group or a cyanoalkylcarbamoyl group, $R^2$ represents a hydrogen atom or group, and the bond represented by ---- represents a single or double bond}.

The present invention also provides an agent for preventing or treating a disease against which a monoamine oxidase inhibition is effective, which comprises an oxazolidone derivative of the above general formula (I) and/or a pharmacologically acceptable salt thereof as the active ingredient.

The present invention further provides a medicinal composition comprising a therapeutic dose of an oxazolidone derivative of the above general formula (I) and/or a pharmacologically acceptable salt thereof and a pharmacologically acceptable excipient; a use of an oxazolidone derivative of the above general formula (I) or a pharmacologically acceptable salt thereof for the preparation of a therapeutic agent for diseases against which a monoamine oxidase inhibition is effective; and a therapeutic method wherein a therapeutic dose of an oxazolidone derivative of the above general formula (I) and/or a pharmacologically acceptable salt thereof is administered to a patient suffering from a disease against which a monoamine oxidase inhibition is effective.

The present invention is useful for treating diseases against which a monoamine oxidase A inhibition is effective, particularly diseases against which the administration of an antidepressant is effective.

The present invention will now be described in detail.

The lower alkyl groups in $R^1$, $R^2$, $R^3$, $R^4$, $R^5$, $R^6$, $R^7$ $R^8$ and $R^9$ in the above general formula (I) are straight chain or branched alkyl groups having 1 to 8 carbon atoms, such as methyl, ethyl, propyl, isopropyl, butyl, isobutyl, sec-butyl, tert-butyl, pentyl (amyl), isopentyl, neopentyl, 1-methylbutyl, 2-methylbutyl, 1,1-dimethylpropyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl- 1-methylpropyl, 1-ethyl-2-methylpropyl, heptyl and octyl groups. Among them, preferred are methyl, ethyl, propyl and isopropyl groups.

The lower alkoxy groups in $R^3$ and $R^4$ are straight-chain or branched alkoxy groups having 1 to 8 carbon atoms such as methoxy, ethoxy, n-propoxy, isopropoxy, n-butoxy, isobutoxy, sec-butoxy, tert-butoxy, 1-methylbutoxy, 2-methylbutoxy, 1,2-dimethylpropoxy and hexyloxy groups. Among them, preferred are methoxy and ethoxy groups.

The alkoxyalkyl groups in the definition of $R^1$ are those derived from the above-described lower alkyl groups.

The aryl groups of the aryl groups which may be substituted in the definition of $R^1$ include phenyl, naphthyl, tolyl and xylyl groups.

The arylalkyl groups of the arylalkyl groups which may be substituted in the definition of $R^1$ are those derived from the above-described aryl groups.

The heteroaryl groups of the heteroaryl groups which may be substituted in the definition of $R^1$ are saturated or unsaturated 5- to 7-membered rings having 1 or 2 nitrogen, sulfur or oxygen atoms.

The heteroarylalkyl groups of the heteroarylalkyl groups which may be substituted in the definition of $R^1$ are those derived from the above-described heteroaryl groups.

The substituents in the "aryl groups which may be substituted", "arylalkyl groups which may be substituted", "heteroaryl groups which may be substituted", and "heteroarylalkyl groups which may be substituted" include hydroxyl, lower alkyl, cyano, lower alkoxy, amino, nitro, carboxyl, hydroxyalkyl, alkoxyalkyl, cyanoalkyl and cyanoalkenyl groups.

The hydroxyalkyl groups in the definition of $R^1$ are the above-described lower alkyl groups which further have one or two hydroxyl groups bonded to any carbon atom of them.

The alkenyl groups of the cyanoalkenyl groups in the definition of $R^1$ correspond to the above-described lower alkyl groups which have one or more double bonds between two carbon atoms thereof. The cyano group may be bonded to any carbon atom of the alkenyl group.

The carbamoylalkyl groups in the definition of $R^1$ are those derived from the above-described lower alkyl groups.

The cyanoalkylcarbamoyl groups in the definition of $R^1$ are those derived from the above-described cyanoalkyl groups.

The halogen atoms in the definition of $R^1$ include fluorine, chlorine, bromine and iodine atoms.

The cycloalkyl groups in the definition of $R^1$ include those having 3 to 10 carbon atoms, such as cyclopropyl, cyclobutyl, cyclopentyl, cyclohexyl, cycloheptyl, cyclooctyl, cyclononyl and cyclodecyl groups.

The term "may form a ring together with the nitrogen atom to which they are bonded" in the definition of $R^5$ and $R^6$, or $R^7$ and $R^8$ refers specifically to piperidino and pyrrolidino groups and, piperidino and morpholino groups which further contain a nitrogen, oxygen or sulfur atom.

Substituents of them include hydroxyl, cyano, carboxyl, amino, nitro, lower alkyl, lower alkoxy, hydroxyalkyl, cyanoalkyl and cyanoalkenyl groups.

The pharmacologically acceptable salts in the present invention include inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as aspartate and glutamate.

Some of these compounds may form salts with metals such as Na, K, Ca and Mg, which are included in the pharmacologically acceptable salts of the present invention.

The compounds of the present invention may form geometrical or optical isomers depending on the substituents, and these isomers are included in the present invention.

Preferred examples of the compounds of the present invention will be given below specifically for facilitating the understanding of the present invention, which by no means limit the invention.

Examples of the most desirable compounds are those of the following general formula (A) and pharmacologically acceptable salts of them:

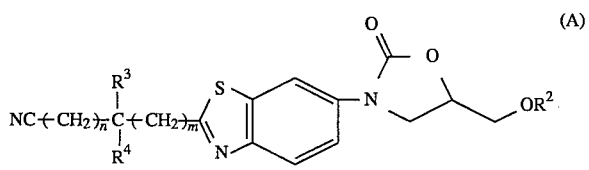

(A)

(wherein $R^2$, $R^3$, $R^4$, n and m are as defined above).

$R^2$ is desirably a hydrogen atom or a methyl, ethyl or n-propyl group, among which a hydrogen atom or methyl group is more desirable and a methyl group is most desirable.

$R^3$ and $R^4$ may be the same or different from each other and each represents desirably a hydrogen atom or a hydroxyl or lower alkyl group, among which a hydrogen atom or a hydroxyl,-methyl, ethyl, n-propyl, n-butyl or t-butyl group is more desirable and a hydrogen atom or a hydroxyl or methyl group is most desirable.

The most desirable combination of $R^3$ and $R^4$ comprises a hydrogen atom and a hydroxyl group. The next most desirable combination of them comprises a hydroxyl group and a lower alkyl group. The still next most desirable combination of them comprises two hydrogen atoms.

n and m represent independently from each other 0 or an integer of 1 to 4. Desirable combinations of n and m comprises n=3 and m=0; n=2 and m=1; n=1 and m=2; n=0 and m=3; n=2 and m=0; n=1 and m=1; and n=0 and m=2, among which more desirable combinations comprises n=3 and m=0; and n=2 and m=0, the most desirable combination comprising n=2 and m=0.

Examples of the next most desirable compounds are those of the following general formula (B) and pharmacologically acceptable salts thereof:

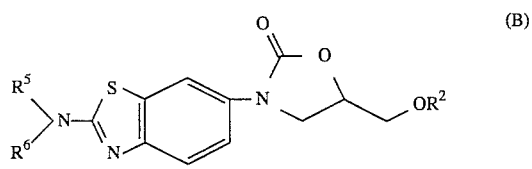

(B)

(wherein $R^2$, $R^5$ and $R^6$ are as defined above).

$R^2$ is desirably a hydrogen atom or a methyl, ethyl or n-propyl group, among which a hydrogen atom and a methyl group are more desirable and a methyl group is most desirable.

$R^5$ and $R^6$ may be preferably the same or different from each other and each represents a hydrogen atom or a cyanoalkyl group, or a case that $R^5$ and $R^6$ form a ring together with the nitrogen atom to which they are bonded, still preferably a case that $R^5$ and $R^6$ form a ring together with the nitrogen atom to which they are bonded, and the ring is specifically a piperidino or pyrrolidino group. The ring may have desirably one or two substituents, more desirably one substituent. Preferred examples of the substituents include cyano, hydroxyl and carboxyl groups.

Examples of the still next most desirable compounds are those of the following general formula (C) and pharmacologically acceptable salts thereof:

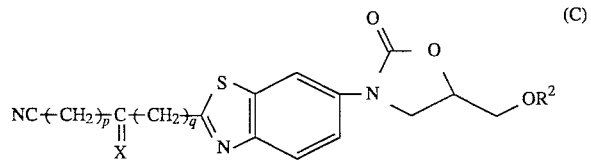

(C)

(wherein $R^2$, X, p and q are as defined above).

$R^2$ is desirably a hydrogen atom or a methyl, ethyl or n-propyl group, among which a hydrogen atom or a methyl group is more desirable and a methyl group is most desirable.

X is desirably a sulfur or oxygen atom and an oxygen atom is most desirable.

p and q independently represent 0 or an integer of 1 to 4. Desirable combinations of p and q comprise p=3 and q=0; p=2 and q=1; p=1 and q=2; p=0 and q=3; p=2 and q=0; p=1 and q=1; and p=0 and q=2, among which more desirable combinations comprise p=8 and q=O; and p=2 and q=0 and the most desirable combination comprises p=2 and q=0.

Among the compounds of the present invention, those having a particularly excellent monoamine oxidase inhibition effect are the following compounds or pharmacologically acceptable salts of them:

1) 3-[2-(1-Hydroxy-3-cyanopropyl)benzothiazol-6-yl]-5-methoxymethyl-2-oxazolidinone, 2) 3-[2-(3-Cyanopropyl)benzothiazol-6-yl]-5-methoxymethyl-2-oxazolidinone, 3) 3-[2-(1-Hydroxy-4-cyanobutyl)benzothiazol-6-yl]-5-methoxymethyl-2-oxazolidinone, and 4) 3-[2-(4-Cyanobutyl)benzothiazol-6-yl]-5-methoxymethyl-2-oxazolidinone.

Typical processes for producing the compounds of the present invention will now be described.

Production process 1

(The first step)

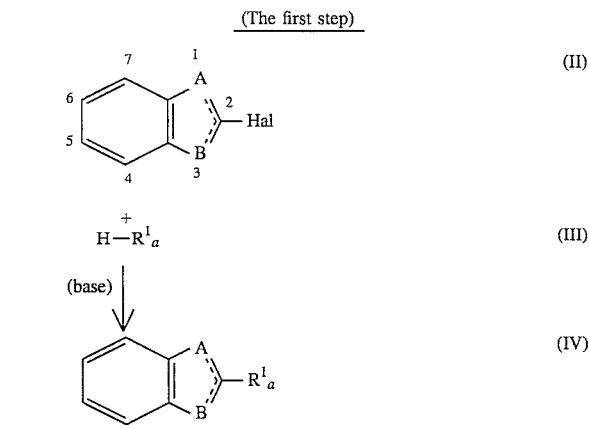

(wherein A and B are as defined above, $R^1_a$ represents a group selected from among those in the above-described definition of $R^1$ excluding halogen atoms and a group of the formula:

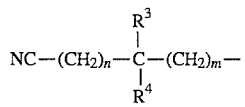

(wherein $R^3$, $R^4$, m and n are as defined above), and Hal represents a halogen atom).

Namely, a compound of the general formula (II) is reacted with a compound of the general formula (III) in the presence or absence of a base to form a compound of the general formula (IV).

Any kind of base may be used. Examples of preferred bases include alkali metal salts such as potassium carbonate and sodium hydrogencarbonate; alkali metal hydrides such as sodium hydride and potassium hydride; and amines such as triethylamine.

The reaction solvent usable herein is any of organic solvents which do not participate in the reaction. Preferred are alcohol solvents such as ethanol; ether solvents such as tetrahydrofuran and dioxane; and dimethylformamide.

The reaction temperature ranges from about 0° C. to the reflux temperature of the solvent.

(The second step)

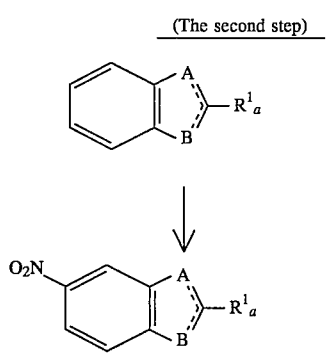

(wherein A B and $R^1_a$ are as defined above).

Namely, the compound of the general formula (IV) obtained in the first step is nitrated in an ordinary manner to form a compound of the general formula (V).

(The third step)

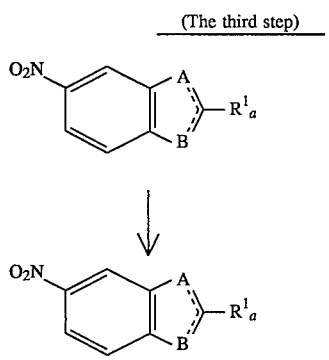

(wherein A, B and $R^1_a$ are as defined above).

Namely, the compound of the general formula (V) obtained in the second step is reduced by ordinary catalytic hydrogenation to form a compound of the general formula (VI).

Preferred catalysts include, for example, palladium-carbon, platinum oxide, Raney nickel and rhodium-alumina.

The reaction solvent usable herein is any of organic solvents which do not participate in the reaction. Preferred are alcohol solvents such as methanol; hydrocarbon solvents such as toluene; ether solvents such as tetrahydrofuran; N,N-dimethylformamide; and ethyl acetate.

The reaction temperature ranges from about 0° C. to the reflux temperature of the solvent.

(The fourth step)

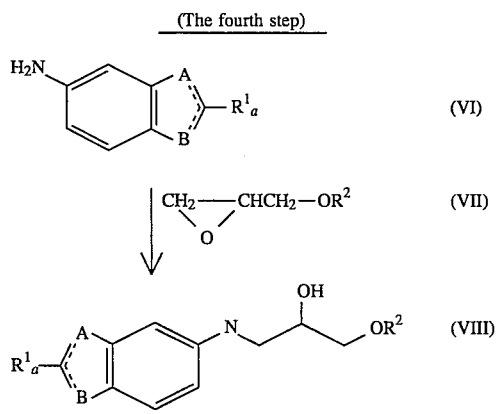

(wherein $R^1_a$, $R^2$, A and B are as defined above).

Namely, the compound of the general formula (VI) obtained in the third step is condensed with a glycidol derivative of the general formula (VII) in an ordinary manner to form a compound of the general formula (VIII).

The compound (VIII) can be produced in a higher yield by using magnesium perchlorate, sodium perchlorate or lithium perchlorate according to a process described in "Tetrahedron Letters", Vol. 31, No. 32, pages 4661 to 4664 (1990).

The reaction solvent may be any organic solvent usually used for organic synthesis so far as it does not participate in the reaction. When no perchlorate is used, an alcoholic solvent such as methanol, ethanol, n-propanol, i-propanol and n-butanol is preferred and, on the contrary, when a perchlorate is used, acetonitrile is preferred.

The reaction temperature ranges from about 0° C. to the reflux temperature of the solvent.

This step can also be conducted by a method in which a sealed tube is used as the case may be.

(The fifth step)

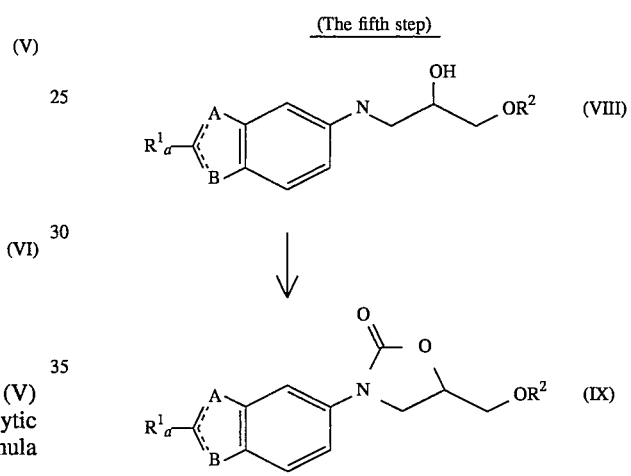

(wherein $R^1_a$, $R^2$, A and B are as defined above).

Namely, the compound of the general formula (VIII) obtained in the fourth step is reacted with a symmetric carbonyl compound such as N,N'-carbonyldiimidazole and diethyl carbonate to form an intended compound (IX) having a cyclic urethane.

The reaction solvent usable herein is any of organic solvents which do not participate in the reaction. Preferred are ether solvents such as tetrahydrofuran.

The reaction temperature ranges from about 0° C. to the reflux temperature of the solvent.

When $R^1$ is a halogen atom, an intended compound (I) can be obtained by starting with the second step.

Production process 2

When an intended compound is one represented by the following general formula (X):

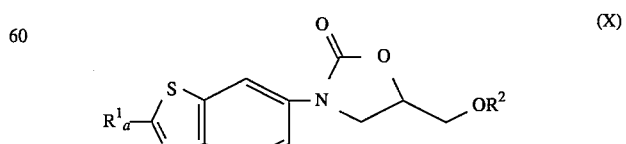

(wherein $R^1_a$ and $R^2$ are as defined above). it can be produced by also the following process:

(The first step)

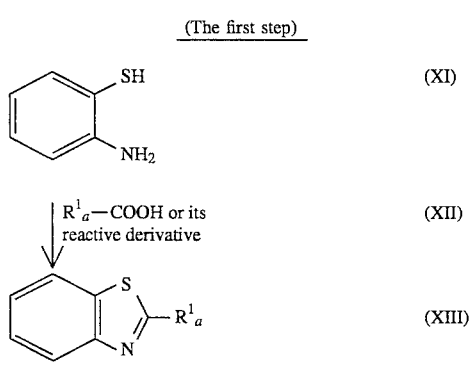

(wherein $R^1_a$ is as defined above).

Namely, o-aminothiophenol (XI) is reacted with a carboxylic acid or a reactive derivative thereof (XII) in an ordinary manner to form a benzothiazole derivative of the general formula (XIII).

Examples of the reactive derivatives of the carboxylic acids include acid halides, esters and nitriles.

The reaction solvent usable herein is any of organic solvents which do not participate in the reaction. Preferred are benzene, tetrahydrofuran, pyridine and chloroform.

The reaction temperature ranges from about −20° C. to the reflux temperature of the solvent.

The resulting benzothiazole derivative (XIII) can be subjected to the reactions in the same manner as that of the second step to the fifth step of the production process 1 to form an intended compound (X).

Production process 3

When the intended compound is one represented by the general formula (XIV):

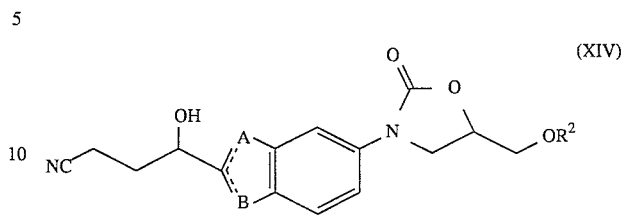

(wherein A, B and $R^2$ are each as defined above), the compound can be synthesized by synthesizing a compound of the general formula (XV):

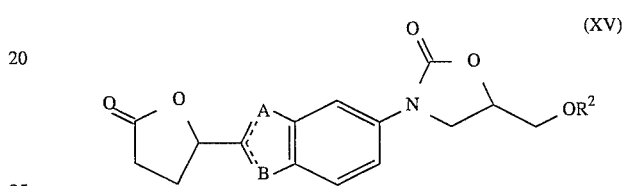

by the production process 2 and followed by the following methods 1 or 2:

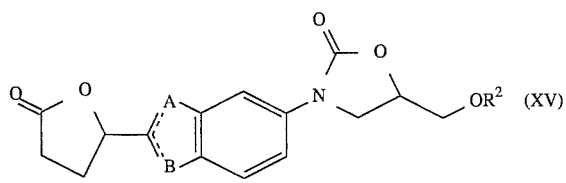

Method 1                    Method 2

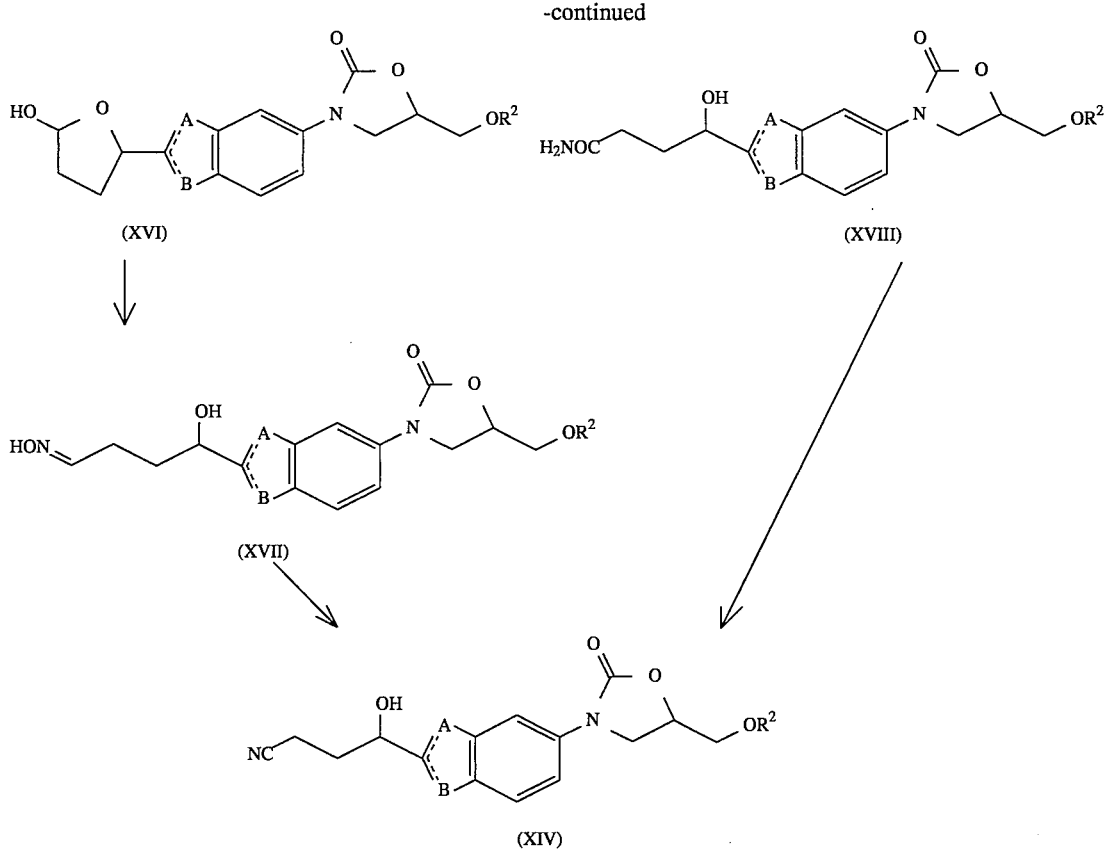

(Method 1)

The compound (XV) is reduced with a metal hydride complex such as lithium tri-t-butoxy aluminum hydride or lithium triethoxy aluminum hydride to reduce only the keto group of the lactone group to thereby form a lactol compound (XVI). Although the reaction temperature may range from ice cooling temperature to the reflux temperature of the solvent, room temperature is preferred. Any solvent usually used for organic synthesis is usable so far as it is inert to the reaction. Examples of particularly preferred solvents include tetrahydrofuran, diethyl ether and 1,2-dimethoxyethane.

The lactol compound (XVI) is reacted with hydroxylamine hydrochloride in a solvent to form an oxime (XVII). Although the reaction temperature may range from ice cooling temperature to the reflux temperature of the solvent, room temperature is preferred. Any solvent usually used for organic synthesis is usable so far as it is inert to the reaction. Examples of particularly preferred solvents include pyridine, water, methanol and ethanol. These solvents can be used either singly or in the form of a mixture of two or more of them.

The oxime (XVII) is reacted with 1-(trifluoroacetyl)imidazole in a solvent to form the intended compound (XIV). Although the reaction temperature ranges from ice cooling temperature to the reflux temperature of the solvent, ice cooling temperature is preferred. Any solvent usually used for organic synthesis is usable so far as it is inert to the reaction. Examples of particularly preferred solvents include liquid ammonia, methanol, ethanol, n-propanol and i-propanol.

(Method 2)

The compound (XV) is reacted with ammonia to form an amide (XVIII). Although the reaction temperature may range from ice cooling temperature to the reflux temperature of the solvent, room temperature is preferred. Any solvent usually used for organic synthesis is usable so far as it is inert to the reaction. Examples of particularly preferred solvents include tetrahydrofuran, diethyl ether and 1,2-dimethoxyethane.

The amide (XVIII) is reacted with trifluoroacetic anhydride in a solvent and then treated with sodium hydrogencarbonate to form the intended compound (XIV). Although the reaction temperature may range from ice cooling temperature to the reflux temperature of the solvent, room temperature is preferred. Any solvent usually used for organic synthesis is usable so far as it is inert to the reaction. Examples of particularly preferred solvents include 1,4-dioxane, tetrahydrofuran and pyridine. They can be used either singly or in the form of a mixture of two or more of them.

Though the main processes for preparing compounds according to the present invention are described above, the compound of the present invention can also be produced by a modification of the above-described main processes, wherein a nitro group is introduced into the benzene ring and then a substituent is introduced at the 2-position thereof.

The substituent at the 2-position can be interchanged by an ordinary method such as oxidation, reduction or condensation.

[Effect of the Invention]

The following Experimental Examples will further illustrate the effect of the present invention.

Experimental Example

Determination of MAO inhibition activity with the use of rat forebrain:

The MAO inhibition activity was determined by a method of Prada et al. (J. Pharmacol. Exp. Ther., 248, 400–414 (1989)).

The enzyme reaction was conducted in 300 μl of a solution having the following composition:

| | |
|---|---|
| enzyme source | 20 μl |
| $^{14}$C-labelled enzyme substrate | 80 μl |
| test compound | 200 μl |
| in total | 300 μl |

The enzyme source used was a suspension of 1 part by volume of the forebrains of male Wistar rats in 5 parts by volume of a 0.1M potassium phosphate buffer (pH 7.4). The enzyme source was mixed with the test compound and the mixture was prewarmed at 37° C. for 10 min. Then the enzyme substrate was added thereto to initiate the enzyme reaction. After 10 min, 200 μl of 2N hydrochloric acid was added to terminate the reaction.

As the substrates for MAO-A and MAO-B, 5-HT (serotonin) and PEA (β-phenethylamine) each labelled with $^{14}$C were used, respectively. The specific radioactivities of 5-HT and PEA were regulated to 11.1 MBq/mmol and 29.6 MBq/mmol, respectively, and the concentrations of them were 200 μM and 20 μM, respectively, in the reaction.

The test compound was dissolved in distilled water so that an intended concentration could be obtained in the enzyme reaction. When the test compound was insoluble in water, it was dissolved in dimethyl sulfoxide to obtain a 10% solution.

Diethyl ether and n-heptane were used as the radioactive metabolites formed by MAO-A and MAO-B, respectively. After the termination of the enzyme reaction, 3 ml of the solvent was added to the reaction mixture and shaken for 10 min. After centrifugation at 3,000 rpm for about 10 min, the lower aqueous layer was frozen in dry ice/acetone. The upper organic layer was recovered by decantation and the radioactivity thereof was determined with a liquid scintillation counter.

The results are given in Tables 1 and 2. The inhibiting activities of the test compounds against MAO A and MAO B are given at the concentrations of $10^{-7}$ M and $10^{-6}$ M or by $IC_{50}$ values.

TABLE 1

| | Inhibiting activity | | | |
|---|---|---|---|---|
| Ex. No. | MAO-A (% at $10^{-7}$M) | | MAO-B (% at $10^{-6}$M) | |
| 1 | | 93 | | 15 |
| 2 | | 64 | | 11 |
| 3 | $IC_{50}$ | 5 nM | | 11 |
| 4 | $IC_{50}$ | 39 nM | | 13 |
| 5 | | 78 | | 11 |
| 7 | | 24 | | 10 |
| 8 | | 80 | | 13 |
| 9 | | 87 | | 13 |
| 13 | $IC_{50}$ | 290 nM | $IC_{50}$ | 598 μM |
| 14 | $IC_{50}$ | 14 nM | $IC_{50}$ | 579 μM |
| 15 | $IC_{50}$ | 256 nM | $IC_{50}$ | 487 μM |
| 16 | | 71 | | 17 |
| 17 | | 24 | | 9 |
| 18 | $IC_{50}$ | 21 nM | $IC_{50}$ | 930 μM |
| 19 | | 61 | | 16 |
| 20 | | 15 | | 14 |
| 21 | | 10 | | 8 |
| 22 | | 75 | | 7 |

TABLE 1-continued

| | Inhibiting activity | | | |
|---|---|---|---|---|
| Ex. No. | MAO-A (% at $10^{-7}$M) | | MAO-B (% at $10^{-6}$M) | |
| 23 | $IC_{50}$ | 28 nM | $IC_{50}$ | >100 μM |
| 24 | $IC_{50}$ | 137 nM | $IC_{50}$ | >100 μM |
| 25 | | 73 | | 7 |
| 26 | | 73 | | 7 |
| 27 | $IC_{50}$ | 6.7 nM | | 10 |
| 28 | $IC_{50}$ | 31 nM | $IC_{50}$ | 990 μM |

TABLE 2

| | Inhibiting activity | | | |
|---|---|---|---|---|
| Ex. No. | MAO-A (% at $10^{-7}$M) | | MAO-B (% at $10^{-6}$M) | |
| 29 | $IC_{50}$ | 19 nM | $IC_{50}$ | 2235 μM |
| 30 | | 42 | | 15 |
| 31 | | 54 | | 12 |
| 32 | | 23 | | 7 |
| 33 | | 5 | | 10 |
| 34 | | 11 | | 8 |
| 35 | | 27 | | 0 |
| 36 | $IC_{50}$ | 6.8 nM | | 1 |
| 37 | $IC_{50}$ | 45 nM | | 35 (at $10^{-5}$M) |
| 38 | | 32 | | 11 |
| 39 | | 15 | | 2 |
| 40 | | 8 | | 6 |
| 41 | | 9 | | 3 |
| 42 | | 63 | | 5 |
| 43 | | 87 (at $10^{-6}$M) | | 14 |
| 44 | | 6 | | 4 |
| 45 | | 40 | | 10 |
| 46 | | 7 | | 3 |
| 47 | | 52 | | 9 |

It is apparent from the above-described experimental examples that the compounds of the present invention are capable of selectively inhibiting MAO-A. Thus the oxazolidone derivatives which are the compounds of the present invention are effective in treating diseases on which MAO inhibition, particularly MAO-A inhibition, is effective. Examples of such diseases include depression, depressive neurosis, and depressive state which is one of the sequelae of cerebrovascular lesion. Further the compounds of the present invention have an excellent antireserpine effect, which improves the therapeutic effect on the above-described diseases.

In addition, the compounds of the present invention have a reduced toxicity and a high safety, so that the present invention is highly valuable also from this viewpoint.

The compounds of the present invention are administered in the form of tablets, powder, granules, capsules, syrup or inhalant as a treating or preventing agent for these diseases. The dose which varies depending on the symptoms, age, kind of disease, etc., is usually about 0.1 to 1,000 mg, desirably 1 to 500 mg, more desirably 1 to 100 mg and most desirably 5 to 50 mg per day for adults, administered at once or in several portions a day.

The preparations containing the compounds are produced with an ordinary pharmaceutical filler by an ordinary method.

Namely, solid oral preparations are produced by adding an excipient and, if necessary, a binder, disintegrator, lubricant, colorant, corrigent, etc. to the active ingredient and forming the mixture into tablets, coated tablets, granules, powder or capsules.

Examples of the excipient include lactose, corn starch, white sugar, glucose, sorbitol, crystalline cellulose and silicon dioxide. Examples of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin. Examples of the lubricant include magnesium stearate, talc, polyethylene glycol, silica and hardened vegetable oils. The colorants are those permitted as medicine additives. The corrigents include cocoa powder, menthol, aromatic powder, mentha oil, borneol and cinnamon powder. These tablets and granules may be suitably coated with sugar, gelatin or the like as a matter of course.

In the production of an injection, a pH regulator, buffer, stabilizer, solubilizer, etc., are added, if necessary, to the active ingredient and a subcutaneous, intramuscular or intravenous injection is produced by an ordinary method.

EXAMPLES

The following Examples will further illustrate the present invention, which by no means limit the invention.

Preparation Examples for the starting compounds also used for the preparation of the intended compounds of the present invention are also given as follows.

In the following Examples, "Me" and "Et" mean a methyl group and a ethyl group, respectively.

Preparation Example 1

2-Hydroxymethylbenzothiazole

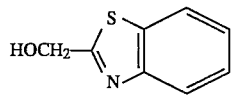

60 g of 2-aminothiophenol and 36.6 g of glycolic acid were heated at 130° C. in a sealed tube for 12 h. The reaction product was dissolved in ethyl acetate and dried over sodium sulfate and the solvent was concentrated under reduced pressure. The residue was crystallized from diisopropyl ether to give 55 g of the titled compound in the form of white crystals.

$^1$H-NMR (CDCl$_3$)δ: 3.54 (1H, t), 5.08 (2H, d), 7.38 (1H, t), 7.47 (1H, t), 7.88 (1H, d), 7.97 (1H, d)

Preparation Example 2

6-Nitro-2-hydroxymethylbenzothiazole

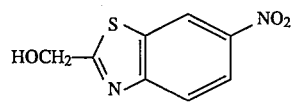

41 g of 2-hydroxymethylbenzothiazole obtained in the Preparation Example 1 was dissolved in 55 ml of concentrated sulfuric acid. 24 ml of concentrated nitric acid (specific gravity: 1.42) was added dropwise to the solution while the reaction temperature was maintained at 40° C. or below. After stirring for 1 h, the reaction mixture was poured into ice-water and extracted with ethyl acetate. The extract was dried over sodium sulfate and then concentrated under reduced pressure to give a solid, which was recrystallized from ethyl acetate to give 15 g of the titled compound.

$^1$H-NMR (CDCl$_3$)δ: 2.37 (1H, s), 5.07 (2H, s), 8.05 (1H, d), 8.35(1H, dd), 8.86 (1H, d)

Preparation Example 3

6-Nitro-2-benzoyloxymethylbenzothiazole

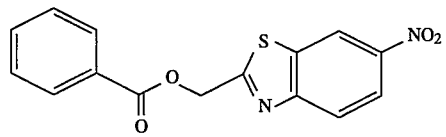

9 ml of benzoyl chloride was added dropwise to a solution of 15 g of the 6-nitro-2-hydroxymethylbenzothiazole obtained in the Preparation Example 2 and 11 ml of triethylamine in tetrahydrofuran at 10° C. The reaction mixture was stirred at room temperature for 1 h and water was added thereto. After extraction with ethyl acetate, the extract was dried over sodium sulfate and concentrated under reduced pressure. The obtained residue was purified by silica gel column chromatography (solvent: dichloromethanol/methanol) to give 10 g of the titled compound.

Preparation Example 4

6-Amino-2-benzoyloxymethylbenzothiazole

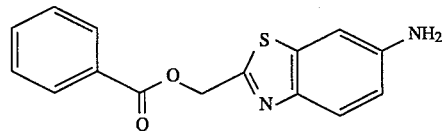

10 g of the 6-nitro-2-benzoyloxymethylbenzothiazole obtained in the Preparation Example 3 was dissolved in a solution comprising a mixture of ethyl acetate and ethanol (1:1) and hydrogenated in the presence of 1 g of a palladium/carbon catalyst for 10 h. After the completion of the reaction, the catalyst was removed by filtration through Celite and the filtrate was concentrated under reduced pressure to give 8.7 g of the titled compound.

Preparation Example 5

N-(2-Benzoyloxymethylbenzothiazol-6-yl)-2-hydroxy-3-methoxypropylamine

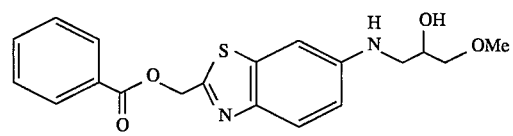

8.7 g of the 6-amino-2-benzoyloxymethylbenzothiazole obtained in the Preparation Example 4 and 3 g of glycidyl methyl ether were refluxed in ethanol for 3 h. The reaction mixture was concentrated under reduced pressure and then purified by silica gel column chromatography (solvent: dichloromethane/methanol) to give 6.2 g of the titled compound.

Preparation Example 6

2-(5-Oxotetrahydrofuran-2-yl)benzothiazole

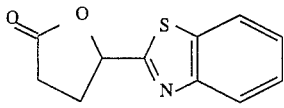

600 of of 2-aminothiophenol was dissolved in 1,500 ml of pyridine. An acid chloride obtained by treating 625 g of (S)-(+)-5-oxo-2-tetrahydrofurancarboxylic acid with thionyl chloride was added dropwise to the solution under cooling with ice. After stirring at room temperature for 3 h, the reaction mixture was poured into ice/water and the precipitates thus formed were separated by filtration and washed with water and then with ether. After recrystallization from acetone and diisopropyl ether, 504 g of the titled compound was obtained.

$^1$H-NMR (CDCl$_3$)δ: 2.6~2.9 (4H, m), 5.8~5.9 (1H, m), 7.45 (1H, t), 7.52 (1H, t), 7.95 (1H, d), 8.04 (1H, d)

Preparation Example 7

6-Nitro-2-(5-oxotetrahydrofuran-2-yl)benzothiazole

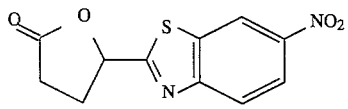

504 g of the 2-(5-oxotetrahydrofuran-2-yl)-benzothiazole obtained in the Preparation Example 6 was dissolved in 2,000 ml of concentrated sulfuric acid. 188 ml of concentrated nitric acid was added dropwise to the solution at −5° to 0° C. and the mixture was stirred under the same conditions for 30 min. After stirring at 0° C. for additional 2 h, the reaction mixture was poured into about 30 l of ice/water. The precipitates thus formed were recovered by filtration, washed with water and then with ethanol and dried to give 488 g of the titled compound.

$^1$H-NMR (CDCl$_3$)δ: 2.6~3.0 (4H, m), 5.8~6.0 (1H, m), 8.13 (1H, d), 8.40 (1H, dd), 8.88 (1H, d)

Preparation Example 8

6-Amino-2-(5-oxotetrahydrofuran-2-yl)benzothiazole

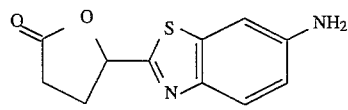

388 g of the 6-nitro-2-(5-oxotetrabydrofuran-2yl)-benzothiazole obtained in the Preparation Example 7 was suspended in 6,000 ml of dioxane and hydrogenated in the presence of 30 g of a 10% palladium/carbon catalyst at room temperature under atmospheric pressure for 48 h.

The catalyst was removed by filtration and the solvent was distilled off. The obtained solid was recrystallized from acetone and diisopropyl ether to give 300 g of the titled compound.

$^1$H-NMR (CDCl$_3$)δ: 2.6~2.9 (4H, m), 5.8~5.9 (1H, m), 7.08 (1H, dd), 7.58 (1H, d), 7.85 (1H,d)

Preparation Example 9

2-Chloro-6-nitrobenzothiazole

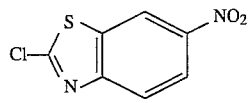

300 g of 2-chlorobenzothiazole was dissolved in 1500 ml of concentrated sulfuric acid and then 134 ml of concentrated nitric acid was added dropwise to the solution at 0° to 10° C. After stirring for 1 h, the reaction mixture was poured into ice/water. The precipitates thus obtained were recovered by filtration, washed with water and then with acetone, and dried to give 380 g of the titled compound.

$^1$H-NMR (CDCl$_3$)δ: 8.07 (1H, d), 8.39 (1H, dd), 8.76 (1H, d)

Preparation Example 10

Ethyl N-(6-nitrobenzothiazol-2-yl)isonipecotate

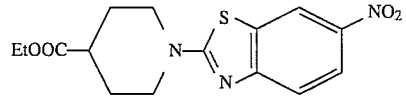

68 g of the 2-chloro-6-nitrobenzothiazole obtained in the Preparation Example 9 and 50 g of ethyl isonipecotate were dissolved in 300 ml of ethanol and 300 ml of tetrahydrofuran. 50 g of sodium hydrogencarbonate was added to the solution, which was heated under reflux for 3 h and poured into ice/water. After extraction with ethyl acetate followed by washing with an aqueous common salt solution, the obtained solution was concentrated under reduced pressure and purified by column chromatography to give 106 g of the titled compound.

$^1$H-NMR (CDCl$_3$)δ: 1.27 (3H, t), 1.8~2.0 (2H, m), 2.0~2.1 (2H, m), 2.6~2.7 (1H, m), 3.3~3.4 (2H, m), 4.1~4.2 (2H, m), 4.18 (2H, quart), 7.50 (1H, d), 8.20 (1H, dd), 8.50 (1H, d)

Preparation Example 11

N-(6-Nitrobenzothiazol-2-yl)isonipecotic acid

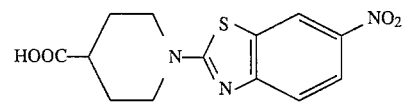

106 g of the ethyl N-(6-nitrobenzothiazol-2-yl)isonipecotate obtained in the Preparation Example 10 was dissolved in 300 ml of ethanol. 150 ml of 5M sodium hydroxide aqueous solution was added to the solution and the mixture was heated for 3 h. The reaction mixture was poured into dilute hydrochloric acid and precipitates thus formed were recovered by filtration, washed with water and then with ether, and dried to give 96 g of the titled compound.

¹H-NMR (CDCl₃)δ: 1.6~1.8 (2H, m), 1.9~2.1 (2H, m), 2.5~2.7 (1H. m), 3.2~3.5 (2H, m), 4.0~4.2 (2H, m), 7.47 (1H, d), 8.13 (1H, dd), 8.70 (1H, d)

Preparation Example 12

N-(6-Nitrobenzothiazol-2-yl)isonipecotamide

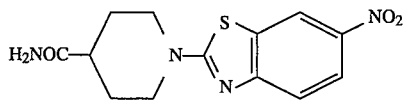

90 g of the N-(6-nitrobenzothiazol-2-yl)isonipecotic acid obtained in the Preparation Example 11 was suspended in 500 ml of tetrahydrofuran and 1,000 ml of dimethylformamide. 100 ml of triethylamine was added to the suspension and 45 ml of isobutyl chlorocarbonate was added dropwise to the suspension under cooling to −20° C. After stirring for 20 min, 100 ml of concentrated aqueous ammonia was added to the mixture at −40° C. and stirred for 20 min. The reaction mixture was poured into ice/water and the formed precipitates were recovered by filtration, washed with water and then with ether, and dried to give 75 g of the titled compound.

¹NMR (d₆-DMSO)δ: 1.5~1.7 (2H, m), 1.9~2.0 (2H, m), 2.5~2.7 (1H, m), 3.2~3.4 (2H, m), 3.9~4.1 (2H,m), 7.47 (1H, d), 8.13 (1H, dd), 8.78 (1H, d)

Preparation Example 13

N-(6-Nitrobenzothiazol-2-yl)-4-cyanopiperidine

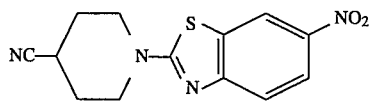

75 g of the N-(6-nitrobenzothiazol-2-yl)isonipecotamide obtained in the Preparation Example 12 was dissolved in 700 ml of dimethylformamide. 50 g of p-toluenesulfonoyl chloride was added to the solution and the mixture was heated at 110° C. for 20 min, poured into ice/water and neutralized with sodium hydroxide. The formed precipitates were recovered by filtration, washed with water and then with ether, and dried to give 60 g of the titled compound.

¹H-NMR (CDCl₃)δ: 2.0~2.2 (4H, m), 3.0~3.1 (1H, m), 3.7~3.8 (2H, m), 3.9~4.0 (2H, m), 7.52 (1H, d), 8.20 (1H, dd), 8.50 (1H, d)

Preparation Example 14

N-(6-Aminobenzothiazol-2-yl)-4-cyanopiperidine

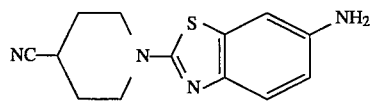

60 g of the N-(6-nitrobenzothiazol-2-yl)-4-cyanopiperidine obtained in the Preparation Example 13 was dissolved in 2,000 ml of dioxane and hydrogenated in the presence of 3 g of a 10% palladium/carbon catalyst at room temperature under atmospheric pressure for 2 h. Then the catalyst was removed by filtration and the solution was concentrated under reduced pressure to give 51 g of the titled compound.

¹H-NMR (CDCl₃)δ: 1.9~2.1 (4H, m), 2.8~3.0 (1H, m), 3.5~3.6 (2H, m), 3.70 (2H, m), 3.7~3.9 (2H, m), 6.70 (1H, dd), 6.95 (1H, d) 7.37 (1H, d)

Example 1

3-(2-Benzoyloxymethylbenzothiazol-6-yl)-5-methoxymethyl-2-oxazolidinone

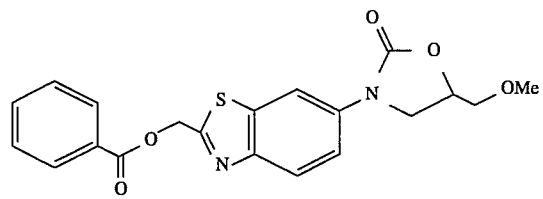

6.2 g of the N-(2-benzoyloxymethylbenzothiazol- 6-yl)-2-hydroxy-3-methoxypropylamine obtained in the Preparation Example 5 and 4 g of carbonyldiimidazole were refluxed in tetrahydrofuran for 3 h. 0.5 ml of water was added dropwise thereto and the solution was refluxed for additional 1 h. The reaction mixture was poured into ice/water. After extraction with ethyl acetate followed by drying over sodium sulfate, the solution was concentrated under reduced pressure. The residue was purified by silica gel column chromatography (solvent: n-hexane/ethyl acetate) to give 4 g of the titled compound.

¹H-NMR (CDCl₃)δ: 3.45 (3H, s), 3.68 (2H, d), 4.03 (1H, dd), 4.14 (1H, t), 4.80 (1H, m), 5.73 (2H, s), 7.49 (2H, m), 7.62 (2H, m), 8.08 (1H, d), 8.13 (2H, m), 8.28 (1H, d)

Example 2

3-(2-Hydroxymethylbenzothiazol-6-yl)-5-methoxymethyl-2-oxazolidinone

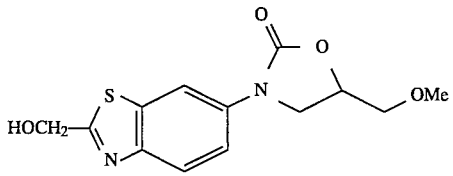

4.7 g of the 3-(2-benzoyloxymethylbenzothiazol-6-yl)-5-methoxymethyl-2-oxazolidinone obtained in the Example 1 was dissolved in methanol/dioxane (1:1) solvent. 7.5 ml of a 2N NaOH aqueous solution was added to the solution and the mixture was stirred for 2 h. Methanol was removed under reduced pressure and then water was added to the residue. After extraction with ethyl acetate followed by drying over sodium sulfate, the solution was concentrated under reduced pressure to give 3.25 g of the titled compound.

¹H-NMR (CDCl₃)δ:3.44 (3H, s), 3.68 (2H, d) 4.02 (1H, dd), 4.14 (1H, t), 4.80 (1H, m), 5.06 (2H, d), 7.52 (1H, 8d), 7.90 (1H, d), 8.21 (1H, d)

Example 3

3-[( 2-Cyanomethyloxymethy]benzothiazol)-6-yl]-5-methoxymethyl-2-oxazolidinone

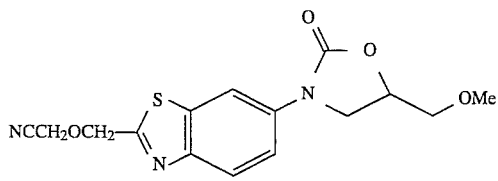

0.6 g of the 3-(2-hydroxymethylbenzothiazol-6-yl)-5-methoxymethyl-2-oxazolidinone obtained in the Example 2, 0.15 ml of bromoacetonitrile and 1.5 ml of 2N aqueous sodium hydroxide-solution were stirred in tetrahydrofuran at room temperature for 3 h. After the addition of water followed by extraction with ethyl acetate and drying over sodium sulfate, the solution was concentrated under reduced pressure. The product was purified by silica gel column chromatography (solvent: hexane/ethyl acetate) to give 0.35 g of the titled compound.

$^1$H-NMR (CDCl$_3$)δ: 3.45 (3H, s), 3.68 (2H, d), 4.02 (1H, t), 4.48 (2H, s), 4.80 (1H, m),5.03 (2H, s), 7.60 (1H, dd), 8.00 (1H, d), 8.28 (1H, d)

Example 4

3-[(2-Cyanomethylaminomethylbenzothiazol)-6-yl]-5-methoxymethyl-2-oxazolidinone

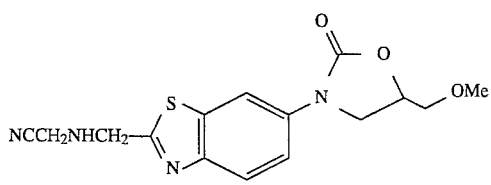

0.6 g of the 3-(2-hydroxymethylbenzothiazol- 6-yl)-5-methoxymethyl-2-oxazolidinone obtained in the Example 2 and 0.47 g of phosphorus pentachloride were stirred in dichloromethane undder cooling with ice for 1 h, poured into ice/water and extracted with ethyl acetate. The organic layer was washed with water, dried over sodium sulfate and concentrated under reduced pressure to give an oily residue, which was dissolved in dimethylformamide. 0.21 g of cyanomethylamine hydrochloride and 0.61 ml of triethylamine were added to the solution, which was stirred under heating at 60° C. for 24 h. After cooling followed by the addition of water and extraction with ethyl acetate, the organic layer was concentrated under reduced pressure and purified by silica gel column chromatography (solvent: dichloromethane/methanol) to give 0.2 g of the titled compound.

$^1$H-NMR (CDCl$_3$)δ: 3.45 (3H, s), 3.68 (2H, d), 3.78 (2H, d), 4.03 (1H, dd), 4.16 (1H, t), 4.37 (2H, d), 4.81 (1H, m), 7.56 (1H, dd), 7.97 (1H, d), 8.28 (1H, d)

Example 5

3-[2-(5-Oxotetrahydrofuran-2-yl)benzothiazol-6-ul]-5methoxymethyl-2-oxazolidinone

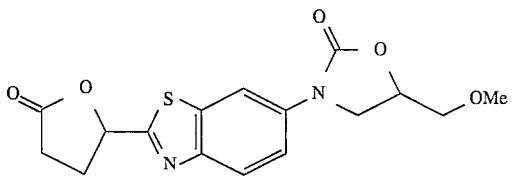

2,000 ml of ethanol was added to 300 g of the 6-amino-2-(5-oxotetrahydrofuran-2-yl)benzothiazole obtained in the Preparation Example 8 and 146 g of (S)-(–)-glycidyl methyl ether and the mixture was heated under reflux for 10 h. The solvent was distilled off under reduced pressure and 8 l of ethyl acetate was added to the residue. The obtained solution was passed through a silica gel column and the eluate was concentrated under reduced pressure to give an oily mixture, which was dissolved in 2,500 ml of tetrahydrofuran. 166 g of 1,1-carbonyldiimidazole was added to the solution and the mixture was heated under reflux for 2 h. Then 200 ml of water was carefully added thereto and the mixture was heated under reflux for 1 h. The reaction liquid was concentrated under reduced pressure into about one-third of the original volume and then poured into ice/water. After extraction with ethyl acetate, the solution was washed with dilute hydrochloric acid, an aqueous sodium hydrogencarbonate solution and an aqueous common salt solution and dried over magnesium sulfate. After concentration under reduced pressure, the product was purified by silica gel column chromatography (methylene chloride/ethanol) to give 166 g of the titled compound.

$^1$H-NMR (CDCl$_3$)δ: 2.6~2.9 (4H, m), 3.43 (3H, s), 3.68 (2H, d), 4.0~4.2 (2H, m), 4.7~5.9 (1H, m), 5.8~5.9 (1H, m), 7.68 (1H, m), 8.00 (1H, d), 8.24 (1H, m)

Example 6

3-[2-(5-Oxotetrahydrofuran-2(S)-yl)benzothiazol-6-yl]-5(R)-methoxymethyl]-2-opxazolidinone

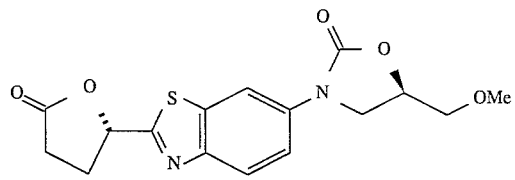

2.1 ml of (S)-(–)-glycidyl methyl ether was dissolved in 25 ml of acetonitrile. 5.2 g of magnesium perchlorate was added to the solution and the mixture was stirred at room temperature for 10 min. 5 g of 6-amino-2-(5-oxotetrahydrofuran-2-yl)benzothiazole obtained in the Preparation Example 8 was added thereto and the resulting mixture was stirred at room temperature for 30 min. Then the reaction liquid was poured into water. After extraction with ethyl acetate, the organic layer was washed with a saturated aqueous common salt solution and dried. The solvent was distilled off to give 6.5 g of an oily residue. The residue was dissolved in 30 ml of tetrahydrofuran. 4.3 g of 1,1-carbonyldiimidazole was added to the solution and the resultant solution was heated under reflux for 1 h. The reaction liquid was cooled and then concentrated under reduced pressure. After solvent replacement with methylene chloride followed by washing with water and drying, the solvent was distilled off under reduced pressure. The resulting residue was purified by silica gel column chromatography and then recrystallized from acetone/isopropyl ether to give 3.8 g of the titled compound.

$^1$H-NMR (CDCl$_3$)δ: 2.6~2.9 (4H, m), 3.43 (3H, s), 3.68 (2H, d), 4.0~4.2 (2H, m), 4.7~4.9 (1H, m), 5.8~5.9 (1H, m), 7.68 (1H, m), 8.00 (1H, d), 8.24 (1H, m)

Example 7

3-[2-(5-Hydroxytetrahydrofuran-2-yl)benzothiazol-6-yl]-5-methoxymethyl]-2oxazolidinone

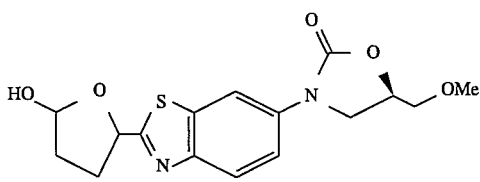

160 g of the 3-[2-(5-oxotetrahydrofuran-2-yl)-benzothiazol-6-yl]-5-methoxymethyl-2-oxazolidinone obtained in the Example 5 was dissolved in 3,000 ml of tetrahydrofuran, and 900 ml of a 1M solution of lithium tri-t-butoxyaluminum hydride in tetrahydrofuran was added dropwise thereto. The mixture was stirred at room temperature for 2 h, poured into ice/water, and neutralized with dilute hydrochloric acid. After extraction with ethyl acetate, the extract was washed with an aqueous sodium hydrogen-carbonate solution, and then with an aqueous common salt solution and dried over magnesium sulfate. After concentration under reduced pressure, the residue was purified by silica gel column chromatography (methylene chloride/ethanol) to give 72 g of the titled compound.

$^1$H-NMR (CDCl$_3$)δ: 2.0~2.8 (4H, m), 3.44 (3H, s), 3.68(2H, d), 4.0~4.2 (2H, m), 4.7~4.9 (1H, m), 5.42 (1/2H, t) , 5.60 (1/2H, quart), 5.73 (1/2H, br. s), 5.85 (1/2H, br. s), 7.5~7.6 (1H, m), 7.9~8.0 (1H, m), 8.2~8.3 (1H, m)

Example 8

3-[2-(1-Hydroxy-3-hydroxyiminopropyl)benzothiazol-6-yl]-5-methoxymethyl-2-oxazolidinone

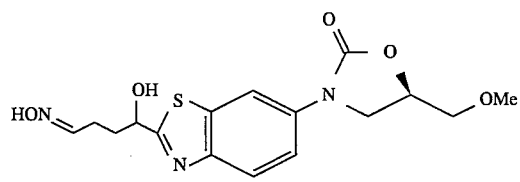

72 g of the 3-[2-(5-hydroxytetrahydrofuran-2-yl)-benzothiazol-6-yl]-5-methoxymethyl-2-oxazolidinone obtained in the Example 7 was dissolved in 150 ml of pyridine. 18.6 g of hydroxylamine hydrochloride was added to the solution at room temperature and the mixture was stirred for 10 min and then poured into ice/water. After extraction with ethyl acetate followed by washing with dilute hydrochloric acid, an aqueous sodium hydrogencarbonate solution and an aqueous common salt solution, the product was dried over magnesium sulfate. After concentration under reduced pressure, the obtained solid was recrystallized from acetone/diisopropyl ether to give 73 g of the titled compound.

$^1$H-NMR (CDCl$_3$)δ: 2.0~2.3 (2H, m), 3.42 (3H, s), 3.6~3.8 (2H, m), 4.0~4.2 (2H, m), 4.8~4.9 (1H, m), 5.0~5.1 (1H, m), 5.85 (1/4H, d), 6.00 (3/4H, d), 7.5~7.7 (1H, m), 7.90(1H, d), 8.20 (1H, d), 10.05 ((3/4H, s), 10.40 (1/4H, s)

Example 9

3-[2-(1(S)-Hydroxy-3-cyanopropyl)benzothiazol-6-yl]-5(R)-methoxymethyl-2-oxazolidinone

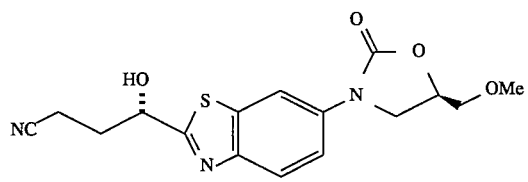

73 g of the 3-[2-(1-hydroxy-3-hydroxyiminopropyl)benzothiazol-6-yl]-5-methoxymethyl-2    -oxazolidinone obtained in the Example 8 was dissolved in 800 ml of tetrahydrofuran. 90 g of trifluoroacetylimidazole was added dropwise to the solution under cooling with ice and the mixture was stirred at room temperature for 4 h. The reaction liquid was poured into an aqueous sodium hydrogencarbonate solution. After extraction with ethyl acetate followed by washing with an aqueous common salt solution, drying over magnesium sulfate and concentration under reduced pressure, the obtained solid was recrystallized from acetone/water to give 51 g of the titled compound.

$^1$H-NMR (CDCl$_3$)δ: 2.1~2.4 (2H, m), 2.5~2.7 (2H, m), 3.42 (3H, s), 3.6~3.7 (2H, m) (3.9~4.1 (2H, m), 3.60 (1H, d), 4.7~4.9 (1H, m), 5.1~5.2 (1H, m), 7.50 (1H, dd), 7.83 (1H, d), 8.15 (1H, d)

m.p.: 74° to 75° C.

Example 10

3-[2-(1(S)-Hydroxy-3-carbamoylpropyl)benzothiazol-6-yl]-5(R)-methoxymethyl-2-oxazolidinone

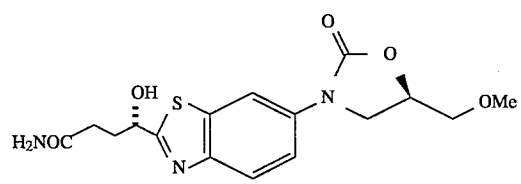

50 ml of liquid ammonia was put in a sealed tube at −78° C. and 2.9 g of 3-[2-(5-hydroxytetrahydrofuran- 2-yl)benzothiazol-6-yl]-5-methoxymethyl-2-oxazolidinone    was added thereto. After sealing followed by stirring at room temperature for 3 h, ammonia was slowly evaporated. Acetone was added to the residue and the precipitated crystals were separated by filtration and dried to give 2.6 g of the titled compound.

¹H-NMR (CDCl₃)δ: 1.90 (1H, m), 2.20 (3H, m), 3.35 (3H, s), 3.60 (2H, m), 3.85 (1H, t), 4.20 (1H, t), 4.80~4.90 (2H, m), 6.25 (1H, d), 6.80 (1H, bs), 7.30 (1H, bs), 7.75 (1H, d), 7.90 (1H, d), 8.20 (1H, s)

m.p.: 170° to 171° C.

Example 11

3[2-(1(S)-Hydroxy-3-cyanopropyl)benzothiazol-6-yl]-5(R)-methoxymethyl-2-oxazolidinone

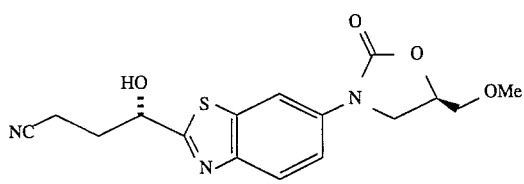

2.0 g of 3-[2-(1(S)-hydroxy-3-carbamoylpropyl)benzothiazol-6-yl]-5(R)-methoxymethyl-2-oxazolidinone was suspended in a liquid mixture of 20 ml of 1,4-dioxane and 3.6 ml of pyridine. 2.0 ml of trifluoroacetic anhydride was added dropwise thereto under cooling with ice for 20 min. The resulting mixture was stirred at room temperature for 2 h and the reaction liquid was added to a saturated aqueous sodium hydrogencarbonate solution. After extraction with ethyl acetate, the organic layer was washed with dilute hydrochloric acid and then with a saturated aqueous common salt solution, and dried. The solvent was distilled off and the resulting residue was crystallized from acetone/water to give 1.6 g of the titled compound.

Example 12

3-[2-(1-hydroxy-4-cyanobutyl)benzothiazol-6-yl]-5-methoxymethyl-2-oxazolidinone

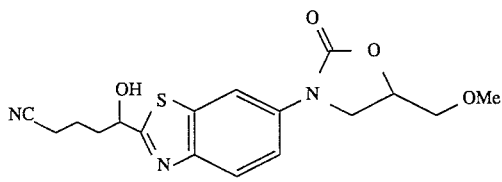

3.48 g of the 3-[2-(5-oxotetrahydrofuran-2-yl)-benzothiazol-6-yl]-5-methoxymethyl-2-oxazolidinone obtained in the Example 5 was dissolved in 20 ml of anhydrous tetrahydrofuran and the solution was cooled to −50° C. 30 ml of a 1.0M solution of diisobutylaluminum hydride in tetrahydrofuran was added dropwise thereto. After stirring for 30 min followed by ordinary treatment and recrystallization, 2.8 g of 3-[2-(1,4-dihydroxybutyl)benzothiazol-6-yl]-5-methoxymethyl-2-oxazolidinone was obtained.

¹H-NMR (CDCl₃)δ: 1.80 (2H, m), 2.00 (2H, m), 3.40 (3H, s), 3.60~3.80 (4H, m), 3.95 (1H, t), 4.10 (1H, t), 4.80 (1, m), 5.10 (1H, m), 7.50 (iH, dd), 7.80 (1H, d), 8.05 (1H, d)

m.p.: 137° to 138° C.

2.8 g of the 3-[2-(1,4-dihydroxybutyl)benzothiazol-6-yl]-5-methoxymethyl-2-oxazolidinone thus obtained was dissolved in 20 ml of anhydrous methylene chloride and 1 ml of anhydrous triethylamine was added to the solution. 0.6 ml of methanesulfonyl chloride was slowly added to the solution under cooling with ice. After stirring for 30 min, 100 ml of diethyl ether was added to the reaction mixture. An insoluble matter was filtered off and then the solvent was distilled off. The resulting crude product was dissolved in 15 ml of dimethyl sulfoxide. 1.5 g of potassium cyanide was added to the solution and a reaction was conducted at 80° C. for 8 h. After cooling the reaction liquid followed by ordinary treatment and purification, 1.5 g of the titled compound was obtained.

¹H-NMR (CDCl₃)δ: 1.90 (2H, m), 2.0~2.2 (2H, m), 2.40 (2H, t), 3.40 (3H, s), 3.65 (2H, m), 4.00 (1H, t), 4.15 (1H, t), 4.80 (1H, m), 5.10 (1H, m), 7.50 (1H, m), 7.90 (1H, t), 8.20 (1H, m)

Example 13

(R)-3-[2-(4-Cyanopiperidino)benzothiazol-6-yl]-5-methoxymethy]-2-oxazolidinone hydrochloride

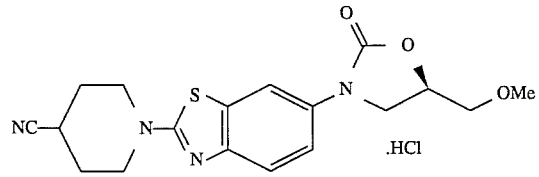

22 g of the N-(6-aminobenzothiazol-2-yl)-4-cyanopiperidine obtained in the Preparation Example 14 and 11.2 ml of (R)-(−)-glycidyl methyl ether were dissolved in 400 ml of ethanol and the solution was heated under reflux for 10 h. After ethanol was removed under reduced pressure, 300 ml of tetrahydrofuran and then 17 g of 1,1'-carbonyldiimidazole were added to the residue and the mixture was heated under reflux for 30 min. Then 50 ml of water was added thereto and the resulting solution was heated under reflux for 30 min. The reaction liquid was concentrated into about one-third of the initial volume and poured into ice/water. After extraction with ethyl acetate followed by washing with water, the product was dried over magnesium sulfate. The solvent was distilled under reduced pressure and the obtained residue was purified by silica gel column chromatography (methylene chloride/ethanol) to give 6.2 g of the titled compound (free).

The product was treated with methanol containing hydrogen chloride to give the titled compound (hydrochloride).

¹H-NMR (free, CDCl₃)δ: 1.9~2.1 (4H, m), 2.9~3.0 (1H, m), 3.42 (3H, s), 3.6~3.7 (4H, m), 3.8~4.1 (4H, m), 4.7~4.8 (1H, m), 7.25 (1H, dd), 7.50 (1H, d), 8.08 (1H, d)

m.p.: 178° to 179° C.

Examples 14 to 52

Compounds listed in Tables 3 to 9 were produced in the same manner as that of the Examples 1 to 13.

TABLE 3

| Ex. No. | Structure | ¹H-NMR spectrum | M.p. (°C.) |
|---|---|---|---|
| 14 | 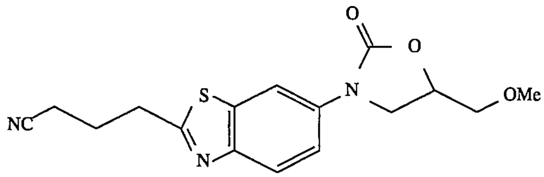 | (CDCl₃) δ:<br>2.30(2H, m), 2.57(2H, t)<br>3.27(2H, t), 3.46(3H, s)<br>3.68(2H, d), 4.03(1H, dd)<br>4.14(1H, t), 4.81(1H, m)<br>7.54(1H, dd), 7.94(1H, d)<br>8.24(1H, d) | 85~87 |
| 15 | 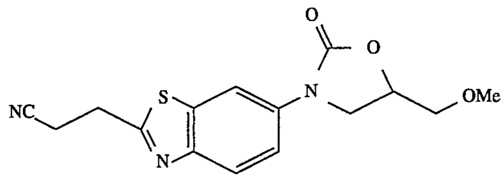 | (CDCl₃) δ:<br>3.00(2H, t), 3.44(2H, t)<br>3.45(3H, s), 3.68(2H, dd)<br>4.02(1H, dd), 4.13(1H, t)<br>4.80(1H, m), 7.55(1H, dd)<br>7.96(1H, d), 8.26(1H, d) | 95~96 |
| 16 | 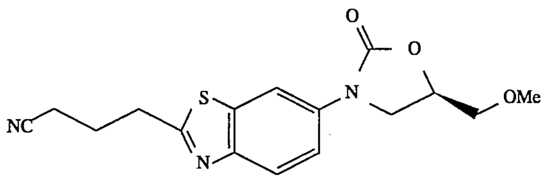 | (CDCl₃) δ:<br>2.23–2.32(2H, m)<br>2.56(2H, t), 3.24(2H, t)<br>3.44(3H, s), 3.66(2H, d)<br>4.04(1H, dd), 4.15(1H, t)<br>4.76~4.83(1H, m)<br>7.55(1H, dd), 7.93(1H, d)<br>8.22(1H, d) | 56~57 |
| 17 | 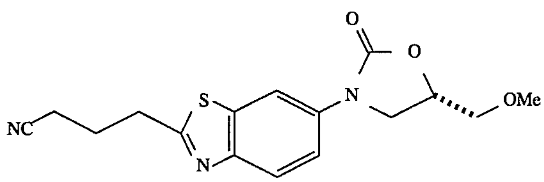 | (CDCl₃) δ:<br>2.28(2H, m), 2.55(2H, t)<br>3.23(2H, t), 3.43(3H, s)<br>3.67(2H, d), 4.01(1H, dd)<br>4.12(1H, t), 4.79(1H, m)<br>7.53(1H, dd), 7.92(1H, d)<br>8.21(1H, d) | — |
| 18 | 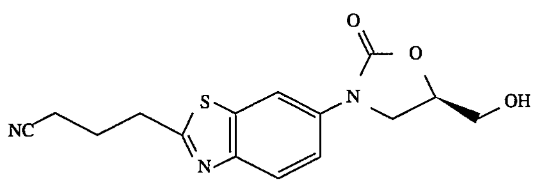 | (CDCl₃) δ:<br>2.24~2.32(2H, m)<br>2.58(2H, t), 3.24(2H, t)<br>3.80(1H, ddd)<br>4.04(1H, ddd)<br>4.10(1H, dd), 4.15(1H, t)<br>4.77~4.83(1H, m)<br>7.54(1H, dd), 7.93(1H, d)<br>8.22(1H, d) | 149 |
| 19 | 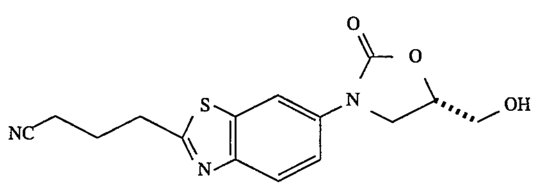 | (DMSO-d₆) δ:<br>2.09(2H, m), 2.63(2H, t)<br>3.16(2H, t)<br>3.5~3.6(1H, m)<br>3.64~3.72(1H, m)<br>3.89(1H, t), 4.13(1H, t)<br>4.68~4.74(1H, m)<br>5.21(1H, t), 7.76(1H, dd)<br>7.91(1H, d), 8.19(1H, s) | 148.5~149 |

TABLE 4

| Ex. No. | Structure | ¹H-NMR spectrum | M.p. (°C.) |
|---|---|---|---|
| 20 | 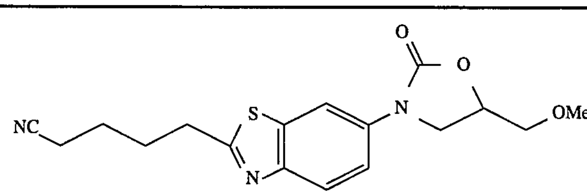 | (CDCl₃) δ:<br>1.83(2H, m), 2.05(2H, m)<br>2.43(2H, t), 3.45(3H, s)<br>3.67(2H, d), 4.02(1H, dd)<br>4.14(1H, t), 4.80(1H, m)<br>7.52(1H, dd), 7.94(1H, d)<br>8.23(1H, d) | 75~76 |

TABLE 4-continued

| Ex. No. | Structure | ¹H-NMR spectrum | M.p. (°C.) |
|---|---|---|---|
| 21 | (benzothiazole with NC-CH₂CH₂-CH=CH- substituent and N-oxazolidinone-CH₂OMe) | (CDCl₃) δ: 2.59(2H, t), 2.67(2H, m) 3.44(3H, s), 3.67(2H, d) 4.02(1H, dd), 4.13(1H, t) 4.78(1H, m), 6.65(1H, m) 8.84(1H, d), 7.53(1H, dd) 7.93(1H, d), 8.23(1H, d) | 63~64 |
| 22 | (benzothiazole with NC-(CH₂)₃- substituent and N-oxazolidinone-CH₂OMe) | (CDCl₃) δ: 1.80(2H, m), 2.03(2H, m) 2.40(2H, t), 3.12(2H, t) 3.41(3H, s), 3.64(2H, d) 3.99(1H, dd), 4.11(1H, t) 4.74~4.81(1H, m) 7.50(1H, dd), 7.90(1H, d) 8.20(1H, d) | — |
| 23 | (benzothiazole with NC-(CH₂)₃- substituent and N-oxazolidinone-CH₂OMe) | (CDCl₃) δ: 1.82(2H, quin) 2.05(2H, quint) 2.42(2H, t), 3.15(2H, t) 3.43(3H, s), 3.68(2H, d) 4.0~4.2(2H, m) 4.7~4.9(1H, m) 7.52(1H, dd), 7.91(1H, d) 8.23(1H, d) | 73~75 |
| 24 | (benzothiazole with NC-(CH₂)₃- substituent and N-oxazolidinone-CH₂OH) | (CDCl₃) δ: 1.79~1.86(2H, m) 2.02~2.10(2H, m) 2.43(2H, t), 3.16(2H, t) 3.80(1H, ddd) 4.04(1H, ddd) 4.09(1H, dd), 4.15(1H, t) 4.76~4.83(1H, m) 7.51(1H, dd), 7.92(1H, d) 8.22(1H, d) | 85~86 |
| 25 | (benzothiazole with NC-CH₂CH₂-C(CH₃)₂- substituent and N-oxazolidinone-CH₂OMe) | (CDCl₃) δ: 1.52(6H, s), 2.22(2H, dd) 2.38(2H, dd), 3.45(3H, s) 3.68(2H, d) 4.0~4.2(2H, m) 4.75~4.82(1H, m) 7.55(1H, dd), 7.95(1H, d) 8.25(1H, d) | 96~97 |

TABLE 5

| Ex. No. | Structure | ¹H-NMR spectrum | M.p. (°C.) |
|---|---|---|---|
| 26 | (benzothiazole with NC-CH₂CH₂-C(CH₃)₂- substituent and N-oxazolidinone-CH₂OH) | (CDCl₃) δ: 1.53(6H, s), 2.22(2H, dd) 2.38(2H, dd) 3.77~3.84(1H, m) 4.0~4.2(3H, m) 4.75~4.83(1H, m) 7.56(1H, dd), 7.96(1H, d) 8.23(1H, d) | 98~99 |

TABLE 5-continued

| Ex. No. | Structure | $^1$H-NMR spectrum | M.p. (°C.) |
|---|---|---|---|
| 27 | (structure) | (CDCl$_3$) δ:<br>2.1~2.4(2H, m)<br>2.5~2.7(2H, m)<br>3.42(3H, s)<br>3.6~3.7(2H, m)<br>3.9~4.1(2H, m)<br>3.60(1H, d)<br>4.7~4.9(1H, m)<br>5.1~5.2(1H, m)<br>7.50(1H, dd), 7.83(1H, d)<br>8.15(1H, d) | oil |
| 28 | (structure) | (CDCl$_3$) δ:<br>2.86(1H, t), 3.29(3H, s)<br>3.45(3H, s), 3.66(2H, d)<br>3.93(2H, t), 3.96(1H, dd)<br>4.09(1H, t)<br>4.74~4.81(1H, m)<br>7.30(1H, dd), 7.52(1H, d)<br>8.08(1H, d) | oil |
| 29 | (structure) | (CDCl$_3$) δ:<br>2.86(2H, t), 3.29(3H, s)<br>3.78(1H, ddd), 3.93(2H, t)<br>3.96~4.05(2H, m)<br>4.09(1H, t)<br>4.73~4.80(1H, m)<br>7.30(1H, dd), 7.52(1H, d)<br>8.05(1H, d) | 120~122 |
| 30 | (structure) | (CDCl$_3$) δ:<br>1.80(2H, m), 2.00(2H, m)<br>3.40(2H, s),<br>3.6~3.8(4H, m)<br>3.95(1H, t), 4.10(1H, t)<br>4.80(1H, m), 5.10(1H, m)<br>7.50(1H, dd), 7.80(1H, d)<br>8.05(1H, d) | 137~138 |
| 31 | (structure) | (CDCl$_3$) δ:<br>2.82(2H, t), 3.43(3H, s)<br>3.68(2H, t), 3.69(2H, t)<br>4.05(1H, dd), 4.16(1H, t)<br>4.78~4.84(1H, m)<br>7.81(1H, dd), 8.16(1H, d)<br>8.28(1H, d) | 141~142 |

TABLE 6

| Ex. No. | Structure | $^1$H-NMR spectrum | M.p. (°C.) |
|---|---|---|---|
| 32 | (structure) | (CDCl$_3$) δ:<br>2.88(2H, t), 3.44(3H, s)<br>3.66(2H, d), 3.82(2H, t)<br>3.96(1H, dd), 4.09(1H, t)<br>4.74~4.81(1H, m)<br>5.45(1H, bs), 7.29(1H, dd)<br>7.52(1H, d), 8.02(1H, d) | 145~146 |
| 33 | (structure) | (CDCl$_3$) δ:<br>2.90(3H, t)<br>3.76~3.90(3H, m)<br>4.00(1H, ddd)<br>4.03(1H, dd), 4.12(1H, t)<br>4.76~4.83(1H, m)<br>7.28(1H, dd), 7.57(1H, d)<br>8.04(1H, d) | 149~150 |

TABLE 6-continued

| Ex. No. | Structure | $^1$H-NMR spectrum | M.p. (°C.) |
|---|---|---|---|
| 34 | 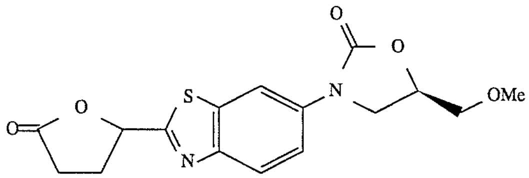 | (CDCl$_3$) δ:<br>2.6~2.9(4H, m)<br>5.8~5.9(1H, m)<br>3.43(3H, s), 7.68(1H, m)<br>3.68(2H, d), 8.00(1H, d)<br>4.0~4.2(2H, m)<br>8.24(1H, m)<br>4.7~4.9(1H, m) | 121~122 |
| 35 | 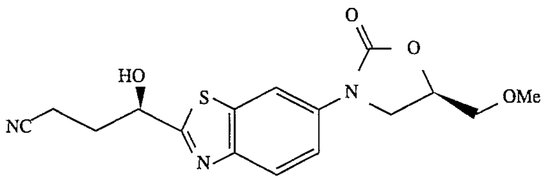 | (CDCl$_3$) δ:<br>2.1~2.4(2H, m)<br>2.5~2..7(2H, m)<br>3.42(3H, s)<br>3.6~3.7(2H, m)<br>3.9~4.1(2H, m)<br>3.60(1H, d)<br>4.7~4.9(1H, m)<br>5.1~5.2(1H, m)<br>7.50(1H, dd), 7.83(1H, d)<br>8.15(1H, d) | 99 |
| 36 | 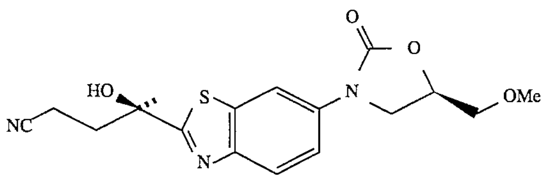 | (CDCl$_3$) δ:<br>1.75(3H, s)<br>2.2~2.6(4H, m)<br>3.45(3H, s), 3.66(2H, d)<br>3.75~3.83(1H, m)<br>4.0~4.2(2H, m)<br>7.58(1H, dd), 7.95(1H, d)<br>8.28(1H, d) | — |
| 37 | 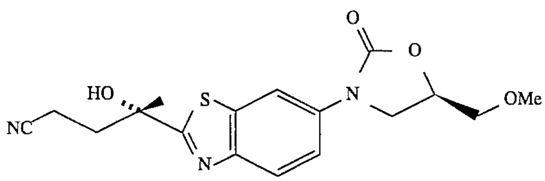 | (CDCl$_3$) δ:<br>1.70(3H, s)<br>2.3~2.6(4H, m)<br>3.40(3H, s), 3.70(2H, m)<br>4.00(1H, dd), 4.10(1H, t)<br>4.80(1H, m), 7.55(1H, dd)<br>7.95(1H, d), 8.25(1H, d) | 90–91 |

TABLE 7

| Ex. No. | Structure | $^1$H-NMR spectrum | M.p. (°C.) |
|---|---|---|---|
| 38 | 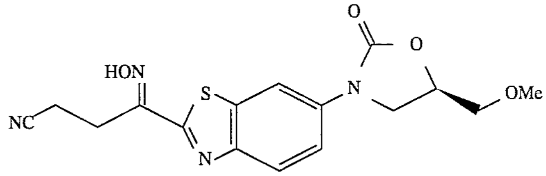 | (CDCl$_3$) δ:<br>2.7~3.0(2H, m)<br>3.34(2H, t), 3.44(3H, s)<br>3.6~3.8(2H, m)<br>4.0~4.3(2H, m)<br>4.8~4.9(1H, m)<br>7.58($^3$/$_5$H, dd)<br>7.77($^2$/$_5$H, dd)<br>7.98($^3$/$_5$H, d)<br>8.08($^2$/$_5$H, d)<br>8.20($^2$/$_5$H, d)<br>8.25($^3$/$_5$H, d) | 139~140 |

TABLE 7-continued

| Ex. No. | Structure | ¹H-NMR spectrum | M.p. (°C.) |
|---|---|---|---|
| 39 | 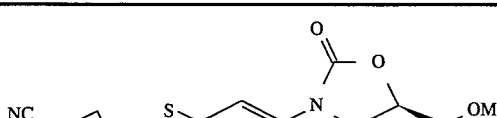 | (CDCl₃) δ: 2.77($^2$/₃H, t) 2.88($^4$/₃H, t) 3.3~3.4(2H, m) 3.42(3H, s) 3.6~3.7(2H, m) 4.0~4.2(2H, m) 4.12(1H, s), 4.20(2H, s) 4.7~4.9(1H, m) 7.60($^1$/₃H, dd) 7.70($^2$/₃H, dd) 7.98($^1$/₃H, d) 8.08($^2$/₃H, d) 8.20($^1$/₃H, d) 8.27($^2$/₃H, d) | 150~151 |
| 40 | 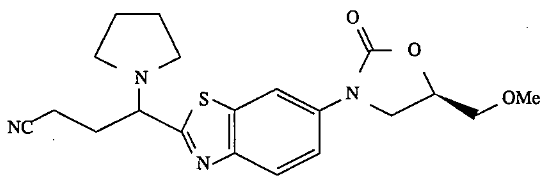 | (CDCl₃) δ: 1.7~1.9(4H, m) 2.2~2.5(4H, m) 2.6~2.8(4H, m) 3.43(3H, s), 3.68(2H, d) 3.9~4.2(3H, m) 4.7~4.9(1H, m) 7.58(1H, dd), 7.97(1H, d) 8.25(1H, d) | 76~77 hydro-chloride |
| 41 | 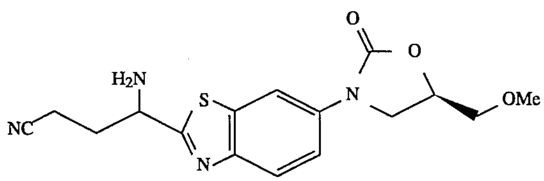 | (CDCl₃) δ: 2.2~2.4(2H, m) 2.5~2.7(2H, m) 3.44(3H, s), 3.67(2H, d) 3.9~4.2(2H, m) 4.7~4.9(1H, m) 7.58(1H, dd), 7.96(1H, d) 8.22(1H, d) | 245~247 fumarate |
| 42 | 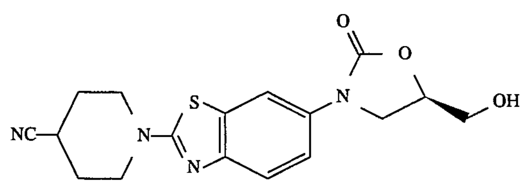 | (DMSO-d₆) δ: 1.80(2H, m), 2.00(2H, m) 3.00(3H, s) 3.20~3.80(6H, m) 4.10(2H, t), 4.70(1H, m) 5.20(1H, t), 7.45(2H, m) 8.00(1H, d) | 178~180 |

TABLE 8

| Ex. No. | Structure | ¹H-NMR spectrum | M.p. (°C.) |
|---|---|---|---|
| 43 | 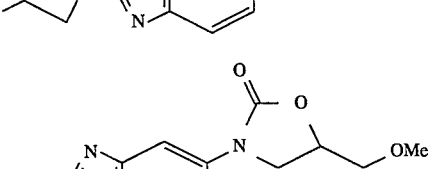 | (CDCl₃) δ: 2.90(4H, t), 3.45(3H, s) 3.65(2H, d), 3.95(4H, t) 3.96(1H, t), 4.10(1H, t) 4.80(1H, m), 7.35(1H, dd) 7.60(1H, d), 8.10(1H, d) | 115~116 |
| 44 | 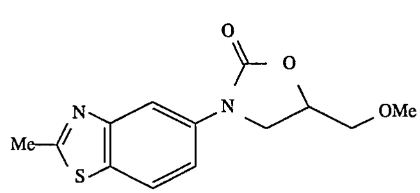 | (CDCl₃) δ: 2.83(3H, s), 3.44(3H, s) 3.68(2H, d), 3.99(1H, dd) 4.12(1H, dd), 4.80(1H, m) 7.79(1H, d), 7.83(1H, d) 7.95(1H, dd) | 139~140 |

TABLE 8-continued

| Ex. No. | Structure | ¹H-NMR spectrum | M.p. (°C.) |
|---|---|---|---|
| 45 | 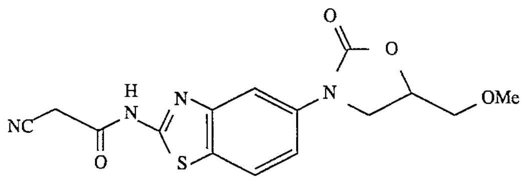 | (CDCl$_3$) δ:<br>3.50(3H, s), 3.57(2H, s)<br>3.6~3.8(2H, m)<br>3.9~4.1(2H, m)<br>4.9~5.0(1H, m)<br>7.10(1H, dd), 7.55(1H, d)<br>7.95(1H, d), 8.94(1H, s) | amorphous |
| 46 | 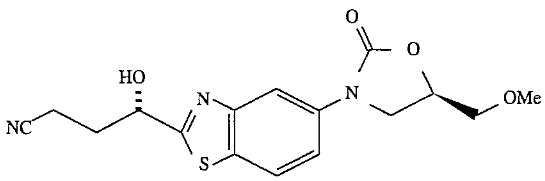 | (CDCl$_3$) δ:<br>2.20(1H, m), 2.40(1H, m)<br>2.60(1H, m), 2.70(1H, m)<br>3.45(3H, s), 3.65(2H, m)<br>3.95(1H, dd), 4.10(1H, t)<br>4.50(1H, br.s)<br>4.80(1H, m), 5.20(1H, m)<br>7.80(2H, s), 7.90(1H, s) | 103~105 |
| 47 | 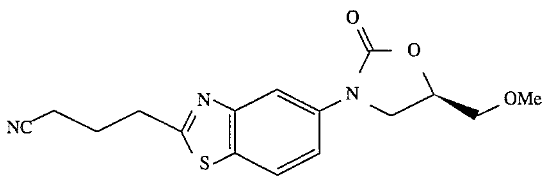 | (CDCl$_3$) δ:<br>2.30(2H, d-t)<br>2.55(2H, t), 3.25(2H, t)<br>3.45(3H, s), 3.70(2H, dd)<br>4.00(1H, dd), 4.15(1H, t)<br>4.80(1H, m), 7.80(1H, dd)<br>7.90(2H, m) | 84~85 |
| 48 | 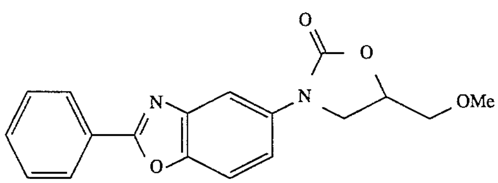 | (DMSO-d$_6$) δ:<br>3.44 (3H, s), 3.68(2H, d)<br>4.0~4.2(2H, m)<br>4.7~4.9(1H, m)<br>7.5~7.6(4H, m)<br>7.7~7.9(2H, m)<br>8.2~8.3(2H, m) | 153~154 |

TABLE 9

| Ex. No. | Structure | ¹H-NMR spectrum | M.p. (°C.) |
|---|---|---|---|
| 49 | 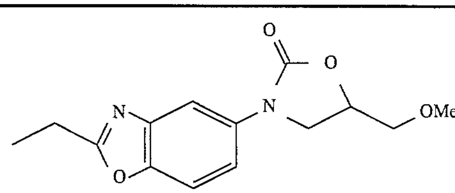 | (CDCl$_3$) δ:<br>1.43(3H, t), 2.97(2H, q)<br>3.44(3H, s), 3.68(2H, m)<br>3.9~4.1(2H, m)<br>4.7~4.9(1H, m)<br>7.4~7.5(1H, d)<br>7.6~7.8(2H, m) | 102~103 |
| 50 | 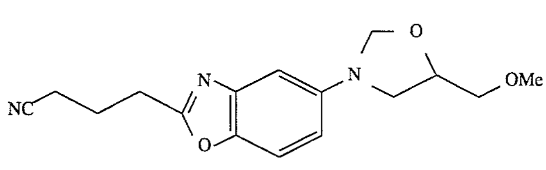 | (CDCl$_3$) δ:<br>2.28(2H, quint)<br>2.60(2H, t), 3.10(2H, t)<br>3.45(3H, s), 3.68(2H, d)<br>3.9~4.1(2H, m)<br>4.7~4.8(1H, m)<br>7.47(1H, d)<br>7.7~7.8(2H, m) | 98~99 |
| 51 | 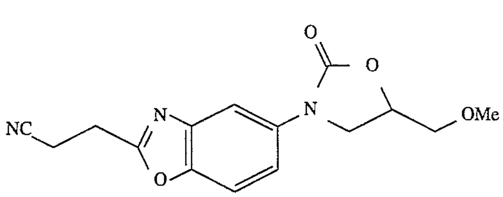 | (CDCl$_3$) δ:<br>3.00(2H, t), 3.32(2H, t)<br>3.45(3H, s), 3.68(2H, d)<br>3.9~4.1(2H, m)<br>4.7~4.8(1H, m)<br>7.50(1H, d)<br>7.7~7.8(2H, m) | 106~107 |

TABLE 9-continued

| Ex. No. | Structure | ¹H-NMR spectrum | M.p. (°C.) |
|---|---|---|---|
| 52 | 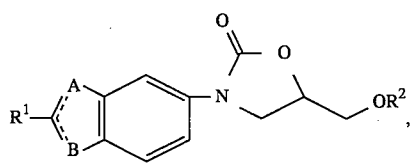 | (CDCl₃) δ:<br>2.40(2H, quint)<br>2.60(2H, t)<br>3.13(2H, t), 3.44(3H, s)<br>3.6–3.7(2H, m)<br>3.9–4.1(2H, m)<br>4.7–4.8(1H, m)<br>7.35(1H, dd)<br>7.64(1H, d), 7.98(1H, d) | 97–98 |

We claim:

1. An oxazolidone derivative represented by the following general formula (I) or a pharmacologically acceptable salt thereof:

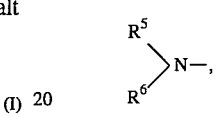 (I)

wherein A and B each represents a nitrogen atom, a sulfur atom or an oxygen atom, with the proviso that at least one of A and B must be a nitrogen atom, $R^1$ represents a hydrogen atom, a halogen atom, a cyano group, a lower alkyl group, a cycloalkyl group having 3 to 10 carbon atoms, benzoyloxymethyl, 1-hydroxy-3-hydroxyiminopropyl, a hydroxyalkyl group, an alkoxyalkyl group, a cyanoalkenyl group, a group represented by the formula:

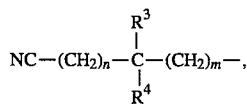

in which n and m each represents 0 or an integer of 1 to 4, and $R^3$ and $R^4$ may be the same or different from each other and each represents a hydrogen atom, a hydroxyl group, a lower alkyl group, a lower alkoxyl group, or a group represented by the formula:

in which $R^7$ and $R^8$ may be the same or different from each other and each represents a hydrogen atom or a lower alkyl group, or $R^7$ and $R^8$ may form a ring together with the nitrogen atom to which they are bonded and the ring may be substituted, a group represented by the formula:

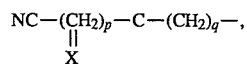

in which p and q each represents 0 or an integer of 1 to 4 and X represents an oxygen atom, a sulfur atom or a group represented by the formula: =N—OR⁹, R⁹ being a hydrogen atom or a lower alkyl group, a group represented by the formula:

$$R^5 \diagdown N-,$$
$$R^6 \diagup$$

in which $R^5$ and $R^6$ may be the same or different from each other and each represents a hydrogen atom, a lower alkyl group or a cyanoalkyl group, or $R^5$ and $R^6$ may form a ring together with the nitrogen atom to which they are bonded and the ring may be substituted, or a group represented by the formula:

NC—(CH₂)ᵣ—Y—(CH₂)ₛ—, in which r and s each represents 0 or an integer of 1 to 4, and Y represents an oxygen atom, a sulfur atom or a group represented by the formula: —NH—, an aryl group which may be substituted, an arylalkyl group which may be substituted, a heteroaryl group which may be substituted, a heteroarylalkyl group which may be substituted, a carbamoylalkyl group or a cyanoalkylcarbamoyl group, wherein heteroalkyl is a saturated or unsaturated 5 to 7-membered ring having 1 or 2 nitrogen, sulfur or carbon atoms, $R^2$ represents a hydrogen atom or a lower alkyl group, and the bond represented by ---- represents a single or double bond.

2. The oxazolidone derivative or the pharmacologically acceptable salt thereof according to claim 1, wherein A represents a sulfur atom and B represents a nitrogen atom.

3. An oxazolidone derivative according to claim 1, represented by the formula

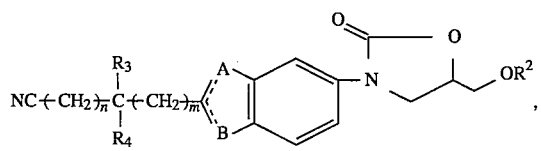

wherein A and B each represents a nitrogen atom, a sulfur atom or an oxygen atom, with the proviso that at least one of A and B must be a nitrogen atom;

n and m each represents 0 or an integer of 1 to 4, and $R^3$ and $R^4$ may be the same or different from each other and each represents a hydrogen atom, a hydroxyl group, a lower alkyl group, a lower alkoxyl group, or a group represented by the formula:

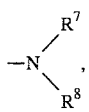

wherein $R^7$ and $R^8$ may be the same or different from each other and each represents a hydrogen atom or a lower alkyl group, or $R^7$ and $R^8$ may form a ring together with the nitrogen atom to which they are bonded and the ring may be substituted; and pharmacologically acceptable salts thereof.

4. An oxazolidone derivative according to claim 3, wherein R is a hydrogen atom, a methyl, ethyl or n-propyl group; $R^3$ and $R^4$ are the same or different from each other and each represents a hydrogen atom, a hydroxyl, methyl, ethyl, n-propyl, n-butyl or t-butyl group.

5. An oxazolidone derivative according to claim 4, wherein $R^3$ and $R^4$ are selected from the group consisting of a hydrogen atom, a hydroxyl group and a methyl group.

6. An oxazolidone derivative according to claim 5, wherein A is a sulfur atom, B is a nitrogen atom.

7. An oxazolidone derivative according to claim 6, selected from the group consisting of 3-[2-(1-hydroxy-3-cyanopropyl)benzothiazol-6-yl]-5-methoxymethyl-2-oxazolidone;

3-[2-(1(S)-hydroxy-3-cyanopropyl)benzothiazol-6-yl]-5(R)-methoxymethyl-2-oxazolidone;

3-[2-(1(R)-hydroxy-3-cyanopropyl)benzothiazol-6-yl]-5(R)-methoxymethyl-2-oxazolidone;

3-[2-(3-cyanopropyl)benzothiazol-6-yl]-5-methoxymethyl-2-oxazolidone;

3-[2-(3-cyanopropyl)benzothiazol-6-yl]-5(R)-methoxymethyl- 2-oxazolidone;

3-[2-(3-cyanopropyl)benzothiazol-6-yl]-5(S)-methoxymethyl- 2-oxazolidone;

3-[2-(1-hydroxy-4-cyanobutyl)benzothiazol-6-yl]-5-methoxymethyl-2-oxazolidone;

3-[2-(4-cyanobutyl)benzothiazol-6-yl]-5-methoxymethyl-2-oxazolidone;

3-[2-(4-cyanobutyl)benzothiazol-6-yl]-5(S)-methoxymethyl-2-oxazolidone;

3-[2-(4-cyanobutyl)benzothiazol-6-yl]-5(R)-methoxymethyl-2-oxazolidone;

3-[2-(2-cyanoethyl)benzothiazol-6-yl]-5-methoxymethyl-2-oxazolidone;

3-[2-(3-cyanopropyl)benzothiazol-6-yl]-5(S)-hydroxymethyl-2 -oxazolidone;

3-[2-(3-cyanopropyl)benzothiazol-6-yl]-5(R)-hydroxymethyl- 2-oxazolidone;

3-[2-(3-(cyano)-1-propenyl)benzothiazol-6-yl ]-5-methoxymethyl-2-oxazolidone;

3-[2-(4-cyanobutyl)benzothiazol-6-yl]-5(S)-hydroxymethyl-2-oxazolidone;

3-[2-(3-(cyano)-1,1-dimethylpropyl)benzothiazol-6-yl ]-5(R)-methoxymethyl-2-oxazolidone;

3-[2-(3-(cyano)-1,1-dimethylpropyl)benzothiazol-6-yl]-5(R)hydroxymethyl-2-oxazolidone;

3-[2-(3-(cyano)-1(R)-hydroxy, 1(S)methyl-propy)benzothiazol- 6-yl]-5(R) -methoxymethyl-2-oxazolidone;

3-[2-(3-(cyano)-1(S)-hydroxy, 1(R)methyl-propyl)benzothiazol- 6-yl]-5(R)-methoxymethyl-2-oxazolidone.

8. An oxazolidone derivative according to claim 3, wherein the compound is 3-[2-(1-amino-3-cyanopropyl-)benzothiazol-6 -yl]-5-methoxymethyl-2-oxazolidone.

9. An oxazolidone derivative according to claim 3, wherein the compound is 3-[2-(1-(1-pyrrolidino)-3-cyanopropyl)benzothiazol-6-yl]-5-methoxymethyl-2-oxazolidone.

10. An oxazolidone derivative according to claim 5, wherein A is a nitrogen atom and B is a nitrogen atom.

11. An oxazolidone derivative according to claim 10, wherein the compound is 2-[2-(1(S)-hydroxy-3-cyanopropyl)benzothiazol-6-yl]-5(R)-methoxymethyl-2-oxazolidone.

12. An oxazolidone derivative according to claim 10, wherein the compound is 2-[2-(3-cyanopropyl)benzothiazol-6-yl]5(R)-methoxymethyl-2-oxazolidone.

13. The oxazolidone derivative or the pharmacologically acceptable salt thereof according to claim 7, wherein A represents a nitrogen atom and B represents a sulfur atom.

14. The oxazolidone derivative or pharmacologically acceptable salt thereof according to claim 1, wherein the compound represented by the general formula (I) is 8-[2-(1-hydroxy-3-cyanopropyl)benzothiazo] -6-yl]-5-methoxymethyi-2-oxazolidinone.

15. The oxazolidone derivative or the pharmacologically acceptable salt thereof according to claim 7, wherein the compound represented by the general formula (I) is 3-[2-(3-cyanopropyl)benzothiazol-6-yl]-5-methoxymethyl-2-oxazolidinone.

16. The oxazolidone derivative or the pharmacologically acceptable salt thereof according to claim 7, wherein the compound represented by the general formula (I) is 3-[2-(1-hydroxy-4-cyanobutyl)benzothiazol-6-yl]-5-methoxymethyl-2-oxazolidinone.

17. The oxazolidone derivative or the pharmacologically acceptable salt thereof according to claim 7, wherein the compound represented by the general formula (I) is 3-[2-(4-cyanobutyl)benzothiazol-6-yl]-5-methoxymethyl-2-oxazolidinone.

18. An agent for treating diseases on which a monoamine oxidase inhibition is effective, which contains the oxazolidone derivative and/or the pharmacologically acceptable salt thereof as set forth in claim 1 as the active ingredient.

19. An agent for treating diseases on which a monoamine oxidase A inhibition is effective, which contains the oxazolidone derivative and/or the pharmacologically acceptable salt thereof as set forth in claim 1 as the active ingredient.

20. An antidepressant containing the oxazolidone derivative and/or the pharmacologically acceptable salt thereof as set forth in claim 1 as the active ingredient.

21. A medicinal composition comprising the oxazolidone derivative and/or the pharmacologically acceptable salt thereof as set forth in claim 1 and a pharmacologically acceptable excipient.

22. A therapeutic method comprising a step of administering a therapeutic dose of the oxazolidone derivative and/or the pharmacologically acceptable salt thereof as set forth in claim 1 to a patient with a disease against which a monoamine oxidase inhibition is effective.

23. A therapeutic method comprising a step of administering a therapeutic dose of the oxazolidone derivative and/or the pharmacologically acceptable salt thereof as set forth in claim 1 to a patient with a disease against which a monoamine oxidase A inhibition is effective.

24. A therapeutic method comprising a step of administering a therapeutic dose of the oxazolidone derivative and/or the pharmacologically acceptable salt thereof as set forth in claim 1 is administered to a patient with a disease against which an antidepressant is effective.

* * * * *

UNITED STATES PATENT AND TRADEMARK OFFICE
CERTIFICATE OF CORRECTION

PATENT NO. : 5 475 014
DATED : December 12, 1995
INVENTOR(S) : Kozo Akasaka et al It is certified that error appears in the above-indentified patent and that said Letters Patent is hereby corrected as shown below:

On the title page, change "[22] Filed Mar. 8, 1994" to
   ---[22] PCT Filed: Sep. 30, 1992
     [86] PCT No.: PCT/JP92/01257
         §371 Date: Mar. 8, 1994
         §102(e) Date: Mar. 8, 1994---.
Col. 42, line 16; change "7" to ---1---.
       line 19; change "1" to ---7---.
       line 20; change "8-[2-" to ---3-[2- ---.
       line 22; change "oxymethyi" to ---oxymethyl---.
       line 64; delete "is administered".

Signed and Sealed this

Eighteenth Day of June, 1996

Attest:

BRUCE LEHMAN

Attesting Officer     Commissioner of Patents and Trademarks